US009856242B2

(12) United States Patent
Kosemund et al.

(10) Patent No.: US 9,856,242 B2
(45) Date of Patent: Jan. 2, 2018

(54) 5-FLUORO-N-(PYRIDIN-2-YL)PYRIDIN-2-AMINE DERIVATIVES CONTAINING A SULFONE GROUP

(71) Applicant: Bayer Pharma Aktiengesellschaft, Berlin (DE)

(72) Inventors: Dirk Kosemund, Berlin (DE); Ulrich Lücking, Berlin (DE); Arne Scholz, Berlin (DE); Gerhard Siemeister, Berlin (DE); Philip Lienau, Berlin (DE)

(73) Assignee: Bayer Pharma Aktiengesellscaft, Berlin (DE)

( * ) Notice: Subject to any disclaimer, the term of this patent is extended or adjusted under 35 U.S.C. 154(b) by 0 days.

(21) Appl. No.: 15/125,659

(22) PCT Filed: Mar. 12, 2015

(86) PCT No.: PCT/EP2015/055146
§ 371 (c)(1),
(2) Date: Sep. 13, 2016

(87) PCT Pub. No.: WO2015/136028
PCT Pub. Date: Sep. 17, 2015

(65) Prior Publication Data
US 2017/0001989 A1 Jan. 5, 2017

(30) Foreign Application Priority Data

Mar. 13, 2014 (EP) ..................................... 14159504

(51) Int. Cl.
A61K 31/444 (2006.01)
C07D 405/14 (2006.01)
(52) U.S. Cl.
CPC .......... *C07D 405/14* (2013.01); *A61K 31/444* (2013.01)
(58) Field of Classification Search
USPC ........................................ 514/332, 333, 335
See application file for complete search history.

(56) References Cited

U.S. PATENT DOCUMENTS

| 2004/0209895 A1 | 10/2004 | Luecking et al. |
| 2005/0176743 A1 | 8/2005 | Luecking et al. |
| 2010/0184789 A1 | 7/2010 | Wabnitz et al. |
| 2011/0028492 A1 | 2/2011 | Barsanti et al. |
| 2011/0306602 A1 | 12/2011 | Wabnitz et al. |

FOREIGN PATENT DOCUMENTS

| EP | 2527332 | 11/2012 | |
| WO | WO-02059110 | 8/2002 | |
| WO | WO-2005037800 | 4/2005 | |
| WO | WO-2006064251 | 6/2006 | |
| WO | WO-2008028590 | 3/2008 | |
| WO | WO-2008060248 | 5/2008 | |
| WO | WO-2008079918 | 7/2008 | |
| WO | WO-2008079933 | 7/2008 | |
| WO | WO 2008/129070 A1 * | 10/2008 | ........... C07D 239/42 |
| WO | WO-2008129070 | 10/2008 | |
| WO | WO-2008129071 | 10/2008 | |
| WO | WO-2008129080 | 10/2008 | |
| WO | WO-2008132138 | 11/2008 | |
| WO | WO-2009029998 | 3/2009 | |
| WO | WO-2009118567 | 10/2009 | |
| WO | WO-2011116951 | 9/2011 | |
| WO | WO-2012117059 | 9/2012 | |
| WO | WO-2013037894 | 3/2013 | |
| WO | WO-2013037896 | 3/2013 | |
| WO | WO 2014/060375 A2 * | 4/2014 | ........... C07D 401/00 |
| WO | WO-2014060376 | 4/2014 | |
| WO | WO-2014076028 | 5/2014 | |
| WO | WO-2014076091 | 5/2014 | |
| WO | WO-2015001021 | 1/2015 | |
| WO | WO-2015136028 | 9/2015 | |

OTHER PUBLICATIONS

Jordan "Tamoxifen . . . " Nature Rev. v.2, p. 205-213 (2003).*
Kirk-Othmer Encyclopedia of Chemical Technology, 8, pp. 95-147 (2002).*
Vippagunta et al., "Crystalline Solids", Advanced Drug Delivery Reviews 48 (2001) 3-26.*
Guillory and Morris (in Brittain ed.), "Polymorphism in Pharmaceutical Solids.," NY: Marcel Dekker, Inc., 1999, 1-2, 125-181, 183-226.*
Yu et al., "Physical characterization of, etc.," PSTT, vl. 1(3), 118-127 (1998).*
Braga et al., "Making crystals from . . . " J. Royal Soc. Chem. Commun. p. 3635-3645 (2005).*
Bernstein, "Polymorphism in . . . " p. 115-118, 272 (2002).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Ivanisevic et al. "Use of X-ray . . . " Pharm. Sci. Encycl. p. 1-42 (2010).*
Seddon "Pseudopolymorph . . . " Crystal Growth & design v.4(6) p. 1087 (2004) (2 pages from internet).*
Jain et al., "Polymorphism in Pharmacy", Indian Drugs, 1986, 23(6) 315-329.*
Dorwald, Side Reactions in Organic Synthesis, 2005, Wiley: VCH Weinheim Preface, pp. 1-15 & Chapter 8, pp. 279-308.*
Allenmark, S. et al. (1983). "Enantioselective Liquid Chromatographic Retention of a Series of Sulfoxides and N-substituted Sulfoximines on Chiral Stationary Phases," *Acta Chemica Scandinavica B* 37: 325-328.
Bark-Jones, S.J. et al. (2006). "EBV EBNA 2 stimulates CDK9-dependent transcription and RNA polymerase II phosphorylation on serine 5," *Oncogene* 25: 1775-1785.

(Continued)

*Primary Examiner* — Pancham Bakshi
(74) *Attorney, Agent, or Firm* — Morrison & Foerster LLP

(57) ABSTRACT

The present invention relates to 5-fluoro-N-(pyridin-2-yl) pyridin-2-amine derivatives containing a sulfone group of general formula (I) as described and defined herein, and methods for their preparation, their use for the treatment and/or prophylaxis of disorders, in particular of hyperproliferative disorders and/or virally induced infectious diseases and/or of cardiovascular diseases. The invention further relates to intermediate compounds useful in the preparation of said compounds of general formula (I).

15 Claims, No Drawings

(56) References Cited

OTHER PUBLICATIONS

Barnes, A.C. et al. (1979). "Pharmacologically Active Sulfoximides: 5-Hexyl-7-(S-methylsulfonimidoyl)xanthone-2-carboxylic Acid, a Potent Antiallergic Agent," *Journal of Medicinal Chemistry* 22(4): 418-424.

Bauer, V.J. et al. (Oct. 1966). "The Reactions of Carbamoyl Azides with Sulfur Nucleophiles," *Journal of Organic Chemisty* 31: 3440-3441.

Berge, S.M. et al. (Jan. 1977). "Pharmaceutical Salts," *Journal of Pharmaceutical Sciences* 66(1): 1-19.

Bolm, C. et al. (1998). "Palladium-Catalyzed Carbon-Nitrogen Bond Formation: A Novel, Catalytic Approach towards N-Arylated Sulfoximines," *Tetrahendron Letters* 39: 5731-5734.

Bolm, C. et al. (2000). "Palladium-Catalyzed N-Arylation of Sulfoximines with Aryl Bromides and Aryl Iodides," *Journal of Organic Chemistry* 65: 169-175.

Bolm, C. et al. (Feb. 2000). "Catalytic Coupling of Aryl Sulfonates with $sp^2$-Hybridized Nitrogen Nucleophiles: Palladium- and Nickel-catalyzed Synthesis of N-Aryl Sulfoximines," *Synthesis* 7: 911-913.

Bolm, C. et al. (2001). "Synthesis of Pseudopeptides with Sulfoximines as Chiral Backbone Modifying Elements," *Chem. Eur. J.* 7(5): 1118-1128.

Bolm, C. et al. (2002). "A Mild Synthetic Procedure for the Preparation of N-Alkylated Sulfoximines," *Synthesis* 7: 879-887.

Cho, G.Y., et al. (2005). "Synthesis and Palladium-Catalyzed Coupling Reaction of Enantiopure p-Bromophenyl Methyl Sulfoximine," *J. Org. Chem.* 70(6): 2346-2349.

Cho, S. et al. (May 1, 2010). "CYCLINg through transcription Posttranslational modification of P-TEFb regulate transcription elongation," *Cell Cycle* 9(9): 1697-1705.

Copeland, R. A. et al. (2006). "Drug-target residence time and its implications for lead optimization," *Nature Reviews Drug Discovery* 5: 730-739.

Craig, D. et al. (1995). "Asymmetric Intramolecular Diels-Alder Reactions of Sulfoximine-activated Trienes," *Tetrahedron* 51(21): 6071-6098.

Cram, D.J. (Dec. 16, 1970). "Stereochemistry of Sulfur Compounds. I. Stereochemical Reactions Cycles Involving an Open Chain Sulfoxide, Sulfimide, and Sulfoximide," *Journal of the American Chemical Society* 92(25): 7369-7384.

De Meijere, A. et al. (2004). "Metal-Catalyzed Cross-Coupling Reactions," *WILEY-VCH Verlag GmbH & Co. KGaA, Weinheim*, pp. 83-91.

Dey, A. et al. (Aug. 1, 2007). "HEXIM1 and the Control of Transcription Elongation from Cancer and Inflammation to AIDS and Cardiac Hypertrophy," *Cell Cycle* 6(15): 1856-1863.

Füger, B. et al. (2009). "Ring-Closing Enyne Metathesis (RCEYM) for the Synthesis of Cyclic Sulfoximines," *Synlett* 10: 1601-1604.

Hackenberger, C.P.R., et al. (2004). "Synthetic and Spectroscopic Investigation of N-Acylated Sulfoximines," *Chem. Eur. J.* 10: 2942-2952.

He, N. et al. (Mar. 14, 2008). "A La-Related Protein Modulates 7SK snRNP Integrity to Suppress P-TEFb-Dependent Transcriptional Elongation and Tumorigenesis," *Molecular Cell* 29: 588-599.

International Search Report dated May 18, 2015 for PCT Application No. PCT/EP2015/055146, filed on Mar. 12, 2015, 3 pages.

Johnson, C.R. (Nov. 4, 1970). "Preparation and Synthetic Applications of (Dimethylamino)phenyloxosulfonium Methylide," *Journal of the American Chemical Society* 92(22): 6594-6598.

Johnson, C.R. (1978). "Preparation of α-Halo Sulfoximines," *Journal of Organic Chemistry* 43(21): 4136-4140.

Johnson, C.R. et al. (1993). "Alkylation of Sulfoximines and Related Compounds at the Imino Nitrogen under Phase-Transfer Conditions," *Journal of Organic Chemistry* 58(7): 1922-1923.

Jones, M.R. et al. (Apr. 3, 1974). "Stereochemisty of Sulfur Compounds. VII. Course of Substitution at Sulfur Attached to Four Different Ligands," *Journal of the American Chemical Society* 96(7): 2183-2190.

Mancheño, O.G. et al. (2007). "Synthesis of N-(1H)-Tetrazole Sulfoximines," *Organic Letters* 9(15): 2951-2954.

Okamura, H. et al. (2004). "Rhodium-Catalyzed Imination of Sulfoxides and Sulfides: Efficient Preparation of N-Unsubstituted Sulfoximines and Sulfilimines," *Organic Letters* 6(8): 1305-1307.

Polla, M.O. et al. (2004). "Design and synthesis of potent, orally active, inhibitors of carboxypeptidase U (TAFIa)," *Bioorganic & Medicinal Chemistry Letters* 12: 1151-1175.

Sammond, D.M. et al. (2005). "Discovery of a novel and potent series of dianilinopyrimidineurea and urea isostere inhibitors of VEGFR2 tyrosine kinase," *Bioorganic & Medicinal Chemistry Letters* 15: 3519-3523.

Sauer, D.T. et al. (1972). "Bis(perfluoroalkyl)sulfur Oxyimines and Silver Bis(trifluoromethyl)sulfur Oxyimine," *Inorganic Chemistry* 11(2): 238-242.

Stoss, P. et al. (1978). "Transannulare Acylwanderungen in cyclischen Sulfoximiden," *Chem. Ber.* 111: 1453-1463.

Wang, S. et al. (2008). "Cyclin-dependent kinase 9: a key transcriptional regulator and potential drug target in oncology, virology and cardiology," *Trends in Pharmacological Sciences* 29(6): 302-313.

Wang, S. et al. (2010). "Discovery and Characterization of 2-Anilino-4-(Thiazol-5-yl)Pyrimidine Transcriptional CDK Inhibitors as Anticancer Agents," *Chemistry & Biology* 17: 1111-1121.

Yang, Z. et al. (Aug. 19, 2005). "Recruitment of P-TEFb for Stimulation of Transcriptional Elongation by the Bromodomain Protein Brd4," *Molecular Cell* 19: 535-545.

Zhou, M. et al. (Dec. 2004). "Coordination of Transcription Factor Phosphorylation and Histone Methylation by the P-TEFb Kinase during Human Inmmunodeficiency Virus Type 1 Transcription," *Journal of Virology* 78(24): 13522-13533.

Zhou, Q. et al. (Sep. 2006). "The Yin and Yang of P-TEFb Regulation: Implications for Human Immunodeficiency Virus Gene Expression and Global Control of Cell Growth and Differentiation," *Microbiology and Molecular Biology Reviews* 70(3): 646-659.

\* cited by examiner

5-FLUORO-N-(PYRIDIN-2-YL)PYRIDIN-2-AMINE DERIVATIVES CONTAINING A SULFONE GROUP

CROSS REFERENCE TO RELATED APPLICATIONS

This application is a National Phase application under 35 U.S.C. §371 of International Application No. PCT/EP2015/055146, filed on Mar. 12, 2015, which claims priority benefit of European Application No. 14159504.1, filed on Mar. 13, 2014, the disclosures of each of which are hereby incorporated by reference in their entireties for all purposes.

The present invention relates to 5-fluoro-N-(pyridin-2-yl) pyridin-2-amine derivatives containing a sulfone group of general formula (I) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I).

The family of cyclin-dependent kinase (CDK) proteins consists of members that are key regulators of the cell division cycle (cell cycle CDK's), that are involved in regulation of gene transcription (transcriptional CDK's), and of members with other functions. CDKs require for activation the association with a regulatory cyclin subunit. The cell cycle CDKs CDK1/cyclin B, CDK2/cyclin A, CDK2/cyclinE, CDK4/cyclinD, and CDK6/cyclinD get activated in a sequential order to drive a cell into and through the cell division cycle. The transcriptional CDKs CDK9/cyclin T and CDK7/cyclin H regulate the activity of RNApolymerase II via phosphorylation of the carboxy-terminal domain (CTD). Positive transcription factor b (P-TEFb) is a heterodimer of CDK9 and one of four cyclin partners, cyclin T1, cyclin K, cyclin T2a or T2b.

Whereas CDK9 (NCBI GenBank Gene ID 1025) is exclusively involved in transcriptional regulation, CDK7 in addition participates in cell cycle regulation as CDK-activating kinase (CAK).

Transcription of genes by RNA polymerase II is initiated by assembly of the pre-initiation complex at the promoter region and phosphorylation of Ser 5 and Ser 7 of the CTD by CDK7/cyclin H. For a major fraction of genes RNA polymerase II stops mRNA transcription after it moved 20-40 nucleotides along the DNA template. This promoter-proximal pausing of RNA polymerase II is mediated by negative elongation factors and is recognized as a major control mechanism to regulate expression of rapidly induced genes in response to a variety of stimuli (Cho et al., Cell Cycle 9, 1697, 2010). P-TEFb is crucially involved in overcoming promoter-proximal pausing of RNA polymerase II and transition into a productive elongation state by phosphorylation of Ser 2 of the CTD as well as by phosphorylation and inactivation of negative elongation factors.

Activity of P-TEFb itself is regulated by several mechanisms. About half of cellular P-TEFb exists in an inactive complex with 7SK small nuclear RNA (7SK snRNA), La-related protein 7 (LARP7/PIP7S) and hexamethylene bis-acetamide inducible proteins 1/2 (HEXIM1/2, He et al., Mol Cell 29, 588, 2008). The remaining half of P-TEFb exists in an active complex containing the bromodomain protein Brd4 (Yang et al., Mol Cell 19, 535, 2005). Brd4 recruits P-TEFb through interaction with acetylated histones to chromatin areas primed for gene transcription. Through alternately interacting with its positive and negative regulators, P-TEFb is maintained in a functional equilibrium: P-TEFb bound to the 7SK snRNA complex represents a reservoir from which active P-TEFb can be released on demand of cellular transcription and cell proliferation (Zhou & Yik, Microbiol Mol Biol Rev 70, 646, 2006). Furthermore, the activity of P-TEFb is regulated by posttranslational modifications including phosphorylation/de-phosphorylation, ubiquitination, and acteylation (reviewed in Cho et al., Cell Cycle 9, 1697, 2010).

Deregulated activity of CDK9 kinase activity of the P-TEFb heterodimer is associated with a variety of human pathological settings such as hyper-proliferative diseases (e.g. cancer), virally induced infectious diseases or cardiovascular diseases:

Cancer is regarded as a hyper-proliferative disorder mediated by a disbalance of proliferation and cell death (apoptosis). High levels of anti-apoptotic Bcl-2-family proteins are found in various human tumors and account for prolonged survival of tumor cells and therapy resistance Inhibition of P-TEFb kinase activity was shown to reduce transcriptional activity of RNA polymerase II leading to a decline of short-lived anti-apoptotic proteins, especially Mcl-1 and XIAP, reinstalling the ability of tumor cells to undergo apoptosis. A number of other proteins associated with the transformed tumor phenotype (such as Myc, NF-kB responsive gene transcripts, mitotic kinases) are either short-lived proteins or are encoded by short-lived transcripts which are sensitive to reduced RNA polymerase II activity mediated by P-TEFb inhibition (reviewed in Wang & Fischer, Trends Pharmacol Sci 29, 302, 2008).

Many viruses rely on the transcriptional machinery of the host cell for the transcription of their own genome. In case of HIV-1, RNA polymerase II gets recruited to the promoter region within the viral LTR's. The viral transcription activator (Tat) protein binds to nascent viral transcripts and overcomes promoter-proximal RNA polymerase II pausing by recruitment of P-TEFb which in turn promotes transcriptional elongation. Furthermore, the Tat protein increases the fraction of active P-TEFb by replacement of the P-TEFb inhibitory proteins HEXIM1/2 within the 7SK snRNA complex. Recent data have shown that inhibition of the kinase activity of P-TEFb is sufficient to block HIV-1 repliction at kinase inhibitor concentrations that are not cytotoxic to the host cells (reviewed in Wang & Fischer, Trends Pharmacol Sci 29, 302, 2008). Similarly, recruitment of P-TEFb by viral proteins has been reported for other viruses such as B-cell cancer-associated Epstein-Barr virus, where the nuclear antigen EBNA2 protein interacts with P-TEFb (Bark-Jones et al., Oncogene, 25, 1775, 2006), and the human T-lymphotropic virus type 1 (HTLV-1), where the transcriptional activator Tax recruits P-TEFb (Zhou et al., J Virol. 80, 4781, 2006).

Cardiac hypertrophy, the heart's adaptive response to mechanical overload and pressure (hemodynamic stress e.g. hypertension, myocardial infarction), can lead, on a long term, to heart failure and death. Cardiac hypertrophy was shown to be associated with increased transcriptional activity and RNA polymerase II CTD phosphorylation in cardiac muscle cells. P-TEFb was found to be activated by dissociation from the inactive 7SK snRNA/HEXIM1/2 complex. These findings suggest pharmacological inhibition of P-TEFb kinase activity as a therapeutic approach to treat cardiac hypertrophy (reviewed in Dey et al., Cell Cycle 6, 1856, 2007).

In summary, multiple lines of evidence suggest that selective inhibition of the CDK9 kinase activity of the P-TEFb heterodimer (=CDK9 and one of four cyclin partners, cyclin T1, cyclin K, cyclin T2a or T2b) represents an innovative approach for the treatment of diseases such as cancer, viral diseases, and/or diseases of the heart. CDK9 belongs to a family of at least 13 closely related kinases of which the subgroup of the cell cycle CDK's fulfills multiple roles in regulation of cell proliferation. Thus, co-inhibition of cell cycle CDKs (e.g. CDK1/cyclin B, CDK2/cyclin A, CDK2/cyclinE, CDK4/cyclinD, CDK6/cyclinD) and of CDK9, is expected to impact normal proliferating tissues such as intestinal mucosa, lymphatic and hematopoietic organs, and reproductive organs. To maximize the therapeutic margin of CDK9 kinase inhibitors, molecules with high selectivity towards CDK9 are required.

CDK inhibitors in general as well as CDK9 inhibitors are described in a number of different publications:

WO2008129070 and WO2008129071 both describe 2,4 disubstituted aminopyrimidines as CDK inhibitors in general. It is also asserted that some of these compounds may act as selective CDK9 inhibitors (WO2008129070) and as CDK5 inhibitors (WO2008129071), respectively, but no specific CDK9 $IC_{50}$ (WO2008129070) or CDK5 $IC_{50}$ (WO2008129071) data is presented. These compounds do not contain a fluoro atom in 5-position of the pyrimidine core.

WO2008129080 discloses 4,6 disubstituted aminopyrimidines and demonstrates that these compounds show an inhibitory effect on the protein kinase activity of various protein kinases, such as CDK1, CDK2, CDK4, CDK5, CDK6 and CDK9, with a preference for CDK9 inhibition (example 80).

WO2005026129 discloses 4,6 disubstituted aminopyrimidines and demonstrates that these compounds show an inhibitory effect on the protein kinase activity of various protein kinases, in particular CDK2, CDK4, and CDK9.

WO 2009118567 discloses pyrimidine and [1,3,5]triazine derivatives as protein kinase inhibitors, in particular CDK2, CDK7 and CDK9.

WO2011116951 discloses substituted triazine derivatives as selective CDK9 inhibitors.

WO2012117048 discloses disubstituted triazine derivatives as selective CDK9 inhibitors.

WO2012117059 discloses disubstituted pyridine derivatives as selective CDK9 inhibitors.

WO2012143399 discloses substituted 4-aryl-N-phenyl-1,3,5-triazin-2-amines as selective CDK9 inhibitors.

EP1218360 B1, which corresponds to US2004116388A1, U.S. Pat. No. 7,074,789B2 and WO2001025220A1, describes triazine derivatives as kinase inhibitors, but does not disclose potent or selective CDK9 inhibitors.

WO2008079933 discloses aminopyridine and aminopyrimidine derivatives and their use as CDK1, CDK2, CDK3, CDK4, CDK5, CDK6, CDK7, CDK8 or CDK9 inhibitors.

WO2011012661 describes aminopyridine derivatives useful as CDK inhibitors.

WO2011026917 discloses carboxamides derived from substituted 4-phenylpyridine-2-amines as inhibitors of CDK9.

WO2012066065 discloses phenyl-heteroaryl amines as inhibitors of CDK9. A selectivity towards CDK9 over other CDK isoforms is preferred, however disclosure of CDK-inhibition data is confined to CDK 9. No bicyclic ring systems are disclosed attached to the C4 position of the pyrimidine core. Within the group attached to C4 of the pyrimidine core, alkoxy phenyls can be regarded as encompassed, but there is no suggestion for a specific substitution pattern characterised by a fluoro atom attached to C5 of the pyrimidine ring, and an aniline at C2 of the pyrimidine, featuring a substituted sulfonyl-methylene group in meta position. Compounds shown in the examples typically feature a substituted cycloalkyl group as $R^1$ but no phenyl.

WO2012066070 discloses 3-(aminoaryl)-pyridine compounds as inhibitors of CDK9. The biaryl core mandatorily consists of two heteroaromatic rings.

WO2012101062 discloses substituted bi-heteroaryl compounds featuring a 2-aminopyridine core as inhibitors of CDK9. The biaryl core mandatorily consists of two heteroaromatic rings.

WO2012101063 discloses carboxamides derived from substituted 4-(heteroaryl)-pyridine-2-amines as inhibitors of CDK9.

WO 2012101064 discloses N-acyl pyrimidine biaryl compounds as inhibitors of CDK9.

WO 2012101065 discloses pyrimidine biaryl compounds as inhibitors of CDK9. The biaryl core mandatorily consists of two heteroaromatic rings.

WO 2012101066 discloses pyrimidine biaryl compounds as inhibitors of CDK9. Substitution $R^1$ of the amino group attached to the heteroaromatic core is confined to non-aromatic groups but does not cover substituted phenyls. Furthermore, the biaryl core mandatorily consists of two heteroaromatic rings.

WO 2011077171 discloses 4,6-disubstituted aminopyrimidine derivatives as inhibitors of CDK9.

WO 2014031937 discloses 4,6-disubstituted aminopyrimidine derivatives as inhibitors of CDK9.

WO 2013037896 discloses disubstituted 5-fluoropyrimidines as selective inhibitors of CDK9.

WO 2013037894 discloses disubstituted 5-fluoropyrimidine derivatives containing a sulfoximine group as selective inhibitors of CDK9.

Wang et al. (Chemistry & Biology 17, 1111-1121, 2010) describe 2-anilino-4-(thiazol-5-yl)pyrimidine transcriptional CDK inhibitors, which show anticancer activity in animal models.

WO 2014060376 discloses substituted 4-(ortho)-fluorophenyl-5-fluoropyrimidin-2-yl amine derivatives containing a sulfone group as selective inhibitors of CDK9.

WO 2014060375 discloses substituted 5-fluoro-N-(pyridin-2-yl)pyridin-2-amine derivatives containing a sulfone group as selective inhibitors of CDK9.

WO 2014060493 discloses substituted N-(pyridin-2-yl) pyrimidin-4-amine derivatives containing a sulfone group as selective inhibitors of CDK9.

WO 2014076028 discloses substituted 4-(ortho)-fluorophenyl-5-fluoropyrimidin-2-yl amine derivatives containing a sulfoximine group as selective inhibitors of CDK9.

WO 2014076091 discloses substituted 5-fluoro-N-(pyridin-2-yl)pyridin-2-amine derivatives containing a sulfoximine group as selective inhibitors of CDK9.

WO 2014076111 discloses substituted N-(pyridin-2-yl) pyrimidin-4-amine derivatives containing a sulfoximine group as selective inhibitors of CDK9.

WO 2015001021 discloses 5-Fluoro-N-(pyridin-2-yl) pyridin-2-amine derivatives containing a sulfoximine group as selective inhibitors of CDK9.

WO2004009562 discloses substituted triazine kinase inhibitors. For selected compounds CDK1 and CDK4 test data, but no CDK9 data is presented.

WO2004072063 describes heteroaryl (pyrimidine, triazine) substituted pyrroles as inhibitors of protein kinases such as ERK2, GSK3, PKA or CDK2.

WO2010009155 discloses triazine and pyrimidine derivatives as inhibitors of histone deacetylase and/or cyclin dependent kinases (CDKs). For selected compounds CDK2 test data is described.

WO2003037346 (corresponding to U.S. Pat. No. 7,618, 968B2, U.S. Pat. No. 7,291,616B2, US2008064700A1, US2003153570A1) relates to aryl triazines and uses thereof, including to inhibit lysophosphatidic acid acyltransferase beta (LPAAT-beta) activity and/or proliferation of cells such as tumor cells.

WO2005037800 discloses sulfoximine substituted anilino-pyrimidines as inhibitors of VEGFR and CDK kinases, in particular VEGFR2, CDK1 and CDK2, having no aromatic ring directly bonded to the pyrimidine ring and having the sulfoximine group directly bonded to the aniline group. No CDK9 data are disclosed.

WO2008025556 describes carbamoyl sulfoximides having a pyrimidine core, which are useful as kinase inhibitors. No CDK9 data is presented. No molecules are exemplified, which possess a fluoropyrimidine core.

WO2002066481 describes pyrimidine derivatives as cyclin dependent kinase inhibitors. CDK9 is not mentioned and no CDK9 data is presented.

WO2008109943 concerns phenyl aminopyri(mi)dine compounds and their use as kinase inhibitors, in particular as JAK2 kinase inhibitors. The specific examples mainly focus on compounds having a pyrimidine core.

WO2009032861 describes substituted pyrimidinyl amines as JNK kinase inhibitors. The specific examples mainly focus on compounds having a pyrimidine core.

WO2011046970 concerns amino-pyrimidine compounds as inhibitors of TBKL and/or IKK epsilon. The specific examples mainly focus on compounds having a pyrimidine core.

WO2012142329 concerns amino-pyrimidine compounds as inhibitors of TBKL and/or IKK epsilon.

WO2012139499 discloses urea substituted anilino-pyrimidines as inhibitors of various protein kinases.

WO2014106762 discloses 4-pyrimidinylamino-benzenesulfonamide derivatives as inhibitors of polo-like kinase-1.

Despite the fact that various inhibitors of CDKs are known, there remains a need for selective CDK9 inhibitors to be used for the treatment of diseases such as hyperproliferative diseases, viral diseases, and/or diseases of the heart, which offer one or more advantages over the compounds known from prior art, such as:
- improved activity and/or efficacy
- beneficial kinase selectivity profile according to the respective therapeutic need
- improved side effect profile, such as fewer undesired side effects, lower intensity of side effects, or reduced (cyto)toxicity
- improved physicochemical properties, such as solubility in water and body fluids
- improved pharmacokinetic properties, allowing e.g. for dose reduction or an easier dosing scheme
- easier drug substance manufacturing e.g. by shorter synthetic routes or easier purification.

A particular object of the invention is to provide CDK9 kinase inhibitors which, compared to the compounds known from prior art, show an increased selectivity for CDK9/Cyclin T1 as compared to CDK2/Cyclin E.

Another object of the invention is to provide CDK9 kinase inhibitors which show an increased potency to inhibit CDK9 activity (demonstrated by a lower $IC_{50}$ value for CDK9/Cyclin T1) compared to the compounds known from prior art.

Another object of the invention is to provide CDK9 kinase inhibitors which show an increased potency to inhibit CDK9 activity at high ATP concentrations compared to the compounds known from prior art.

Another object of the invention is to provide CDK9 kinase inhibitors, which show an improved anti-proliferative activity in tumor cell lines such as HeLa, HeLa-MaTu-ADR, NCI-H460, DU145, Caco-2, B16F10 or A2780, compared to the compounds known from prior art.

Further, it is also an object of the present invention to provide CDK9 kinase inhibitors, which, compared to the compounds known from prior art, are highly selective for CDK9/Cyclin T1 as compared to CDK2/Cyclin E, and/or which show an increased potency to inhibit CDK9 activity and/or which show an improved anti-proliferative activity in tumor cell lines such as HeLa, HeLa-MaTu-ADR, NCI-H460, DU145, Caco-2, B16F10 or A2780, and/or which show an increased potency to inhibit CDK9 activity at high ATP concentrations compared to the compounds known from prior art.

The present invention relates to compounds of general formula (I)

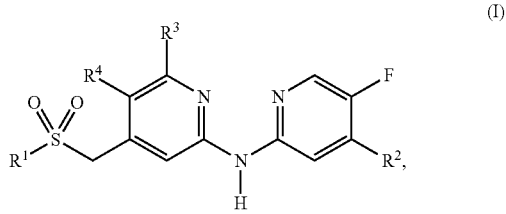

wherein
$R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- or heteroaryl-$C_1$-$C_3$-alkyl-,
  wherein said group is optionally substituted with one or two or three substituents, identically or differently, selected from the group of hydroxy, cyano, halogen, $C_1$-$C_6$-alkyl-, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines, —OP(O)(OH)$_2$, —C(O)OH, —C(O)NH$_2$;

$R^2$ represents the group

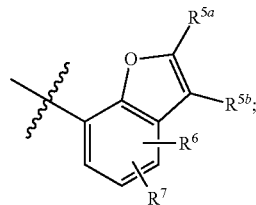

$R^3$, $R^4$ represent, independently from each other, a group selected from a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-;

$R^{5a}$, $R^{5b}$ represent, independently from each other, a group selected from a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-;

R⁶, R⁷ represent, independently from each other, a group selected from a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-;

or their salts, solvates or salts of solvates.

Compounds according to the invention are the compounds of the formula (I) and the salts, solvates and solvates of the salts thereof, the compounds of the hereinafter recited formula which are encompassed by formula (I) and the salts, solvates and solvates of the salts thereof, and the compounds which are encompassed by formula (I) and are mentioned hereinafter as exemplary embodiments and the salts, solvates and solvates of the salts thereof, where the compounds which are encompassed by formula (I) and are mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds according to the invention can be in tautomeric forms, the present invention encompasses all tautomeric forms.

Further, the compounds of the present invention can exist in free form, e.g. as a free base, or as a free acid, or as a zwitterion, or can exist in the form of a salt. Said salt may be any salt, either an organic or inorganic addition salt, particularly any physiologically acceptable organic or inorganic addition salt, customarily used in pharmacy.

Salts which are preferred for the purposes of the present invention are physiologically acceptable salts of the compounds according to the invention. However, salts which are not suitable for pharmaceutical applications per se, but which, for example, can be used for the isolation or purification of the compounds according to the invention, are also comprised.

The term "physiologically acceptable salt" refers to a relatively non-toxic, inorganic or organic acid addition salt of a compound of the present invention, for example, see S. M. Berge, et al. "Pharmaceutical Salts," J. Pharm. Sci. 1977, 66, 1-19.

Physiologically acceptable salts of the compounds according to the invention encompass acid addition salts of mineral acids, carboxylic acids and sulfonic acids, for example salts of hydrochloric acid, hydrobromic acid, hydroiodic, sulfuric acid, bisulfuric acid, phosphoric acid, nitric acid or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Physiologically acceptable salts of the compounds according to the invention also comprise salts of conventional bases, such as, by way of example and by preference, alkali metal salts (for example sodium and potassium salts), alkaline earth metal salts (for example calcium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl)aminomethane, aminopropanediol, Sovak base, and 1-amino-2,3,4-butanetriol. Additionally, the compounds according to the invention may form salts with a quarternary ammonium ion obtainable e.g. by quarternisation of a basic nitrogen containing group with agents like lower alkylhalides such as methyl-, ethyl-, propyl-, and butylchlorides, -bromides and -iodides; dialkylsulfates like dimethyl-, diethyl-, dibutyl- and diamylsulfates, long chain halides such as decyl-, lauryl-, myristyl- and stearylchlorides, -bromides and -iodides, aralkylhalides like benzyl- and phenethylbromides and others. Examples of suitable quarternary ammonium ions are tetramethylammonium, tetraethylammonium, tetra(n-propyl)ammonium, tetra (n-butyl) ammonium, or N-benzyl-N, N, N-trimethylammonium.

The present invention includes all possible salts of the compounds of the present invention as single salts, or as any mixture of said salts, in any ratio.

Solvates is the term used for the purposes of the invention for those forms of the compounds according to the invention which form a complex with solvent molecules by coordination in the solid or liquid state. Hydrates are a special form of solvates in which the coordination takes place with water. Hydrates are preferred as solvates within the scope of the present invention.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^2H$ (deuterium), $^3H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^3H$ or $^{14}C$ are incorporated, are useful in drug and/or substrate tissue distribution studies. Tritiated and carbon-14, i.e., $^{14}C$, u isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

In addition, the present invention also encompasses prodrugs of the compounds according to the invention. The term "prodrugs" encompasses compounds which themselves may be biologically active or inactive, but are converted (for example by metabolism or hydrolysis) to compounds according to the invention during their residence time in the body.

Furthermore, the present invention includes all possible crystalline forms, or polymorphs, of the compounds of the present invention, either as single polymorphs, or as a mixture of more than one polymorphs, in any ratio.

Accordingly, the present invention includes all possible salts, polymorphs, metabolites, hydrates, solvates, prodrugs (e.g.: esters) thereof, and diastereoisomeric forms of the compounds of the present invention as single salt, polymorph, metabolite, hydrate, solvate, prodrug (e.g.: esters) thereof, or diastereoisomeric form, or as mixture of more than one salt, polymorph, metabolite, hydrate, solvate, prodrug (e.g.: esters) thereof, or diastereoisomeric form in any ratio.

For the purposes of the present invention, the substituents have the following meaning, unless otherwise specified:

The terms "halogen", "halogen atom" or "halo" represent fluorine, chlorine, bromine and iodine, particularly bromine, chlorine or fluorine, preferably chlorine or fluorine, more preferably fluorine.

The term "alkyl" represents a linear or branched alkyl radical having the number of carbon atoms specifically indicated, e.g. $C_1$-$C_{10}$ one, two, three, four, five, six, seven, eight, nine or ten carbon atoms, e.g. methyl, ethyl, n-propyl, isopropyl, n-butyl, isobutyl, sec-butyl, tert-butyl, pentyl, isopentyl, hexyl, heptyl, octyl, nonyl-, decyl-, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl. If the number of carbon atoms is not specifically indicated the term "alkyl" represents a linear or branched alkyl radical having, as a rule, 1 to 9, particularly 1 to 6, preferably 1 to 4 carbon atoms. Particularly, the alkyl group has 1, 2, 3, 4, 5 or 6 carbon atoms ("$C_1$-$C_6$-alkyl"), e.g. methyl, ethyl, n-propyl-, isopropyl, n-butyl, tert-butyl, pentyl, isopentyl, hexyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl. Preferably, the alkyl group has 1, 2 or 3 carbon atoms ("$C_1$-$C_3$-alkyl"), methyl, ethyl, n-propyl or isopropyl.

The term "$C_3$-$C_7$-cycloalkyl" is to be understood as preferably meaning a saturated or partially unsaturated, monovalent, monocyclic hydrocarbon ring which contains 3, 4, 5, 6 or 7 carbon atoms. Said $C_3$-$C_7$-cycloalkyl group is for example, a monocyclic hydrocarbon ring, e.g. a cyclopropyl, cyclobutyl, cyclopentyl, cyclohexyl or cycloheptyl group. Said cycloalkyl ring can optionally contain one or more double bonds e.g. cycloalkenyl, such as a cyclopropenyl, cyclobutenyl, cyclopentenyl, cyclohexenyl or cycloheptenyl group, wherein the bond between said ring with the rest of the molecule may be to any carbon atom of said ring, be it saturated or unsaturated. Particularly, said cycloalkyl group is a $C_3$-$C_5$-cycloalkyl, a $C_5$-$C_6$-cycloalkyl or a cyclohexyl group.

The term "$C_3$-$C_5$-cycloalkyl" is to be understood as preferably meaning a saturated, monovalent, monocyclic hydrocarbon ring which contains 3, 4 or 5 carbon atoms. In particular said $C_3$-$C_5$-cycloalkyl group is a monocyclic hydrocarbon ring such as a cyclopropyl, cyclobutyl or cyclopentyl group. Preferably said "$C_3$-$C_5$-cycloalkyl" group is a cyclopropyl group.

The term "$C_3$-$C_6$-cycloalkyl" is to be understood as preferably meaning a saturated, monovalent, monocyclic hydrocarbon ring which contains 3, 4, 5 or 6 carbon atoms. In particular said $C_3$-$C_5$-cycloalkyl group is a monocyclic hydrocarbon ring such as a cyclopropyl, cyclobutyl, cyclopentyl or cyclohexyl group.

The term "heterocyclyl" is to be understood as meaning a saturated or partially unsaturated, monovalent, mono- or bicyclic hydrocarbon ring which contains 3, 4, 5, 6, 7, 8 or 9 carbon atoms and further containing 1, 2 or 3 heteroatom-containing groups selected from oxygen, sulfur, nitrogen. Particularly, the term "heterocyclyl" is to be understood as meaning a "4- to 10-membered heterocyclic ring".

The term "a 4- to 10-membered heterocyclic ring" is to be understood as meaning a saturated or partially unsaturated, monovalent, mono- or bicyclic hydrocarbon ring which contains 3, 4, 5, 6, 7, 8 or 9 carbon atoms, and further containing 1, 2 or 3 heteroatom-containing groups selected from oxygen, sulfur, nitrogen.

A $C_3$-$C_9$-heterocyclyl is to be understood as meaning a heterocyclyl which contains at least 3, 4, 5, 6, 7, 8 or 9 carbon atoms and additionally at least one heteroatom as ring atoms. Accordingly in case of one heteroatom the ring is 4- to 10-membered, in case of two heteroatoms the ring is 5- to 11-membered and in case of three heteroatoms the ring is 6- to 12-membered.

Said heterocyclic ring is for example, a monocyclic heterocyclic ring such as an oxetanyl, azetidinyl, tetrahydrofuranyl, pyrrolidinyl, 1,3-dioxolanyl, imidazolidinyl, pyrazolidinyl, oxazolidinyl, isoxazolidinyl, 1,4-dioxanyl, pyrrolinyl, tetrahydropyranyl, piperidinyl, morpholinyl, 1,3-dithianyl, thiomorpholinyl, piperazinyl, or chinuclidinyl group. Optionally, said heterocyciclic ring can contain one or more double bonds, e.g. 4H-pyranyl, 2H-pyranyl, 2,5-dihydro-1H-pyrrolyl, 1,3-dioxolyl, 4H-1,3,4-thiadiazinyl, 2,5-dihydrofuranyl, 2,3-dihydrofuranyl, 2,5-dihydrothienyl, 2,3-dihydrothienyl, 4,5-dihydrooxazolyl, 4,5-dihydroisoxazolyl, or 4H-1,4-thiazinyl group, or, it may be benzo fused.

Particularly a $C_3$-$C_7$-heterocyclyl is to be understood as meaning a heterocyclyl which contains at least 3, 4, 5, 6, or 7 carbon atoms and additionally at least one heteroatom as ring atoms. Accordingly in case of one heteroatom the ring is 4- to 8-membered, in case of two heteroatoms the ring is 5- to 9-membered and in case of three heteroatoms the ring is 6- to 10-membered.

Particularly a $C_3$-$C_6$-heterocyclyl is to be understood as meaning a heterocyclyl which contains at least 3, 4, 5 or 6 carbon atoms and additionally at least one heteroatom as ring atoms. Accordingly in case of one heteroatom the ring is 4- to 7-membered, in case of two heteroatoms the ring is 5- to 8-membered and in case of three heteroatoms the ring is 6- to 9-membered.

Particularly, the term "heterocyclyl" is to be understood as being a heterocyclic ring which contains 3, 4 or 5 carbon atoms, and 1, 2 or 3 of the above-mentioned heteroatom-containing groups (a "4- to 7-membered heterocyclic ring"), more particularly said ring can contain 4 or 5 carbon atoms, and 1, 2 or 3 of the above-mentioned heteroatom-containing groups (a "5- to 7-membered heterocyclic ring"), more particularly said heterocyclic ring is a "6-membered heterocyclic ring", which is to be understood as containing 4 carbon atoms and 2 of the above-mentioned heteroatom-containing groups or 5 carbon atoms and one of the abovementioned heteroatom-containing groups, preferably 4 carbon atoms and 2 of the above-mentioned heteroatom-containing groups.

The term "$C_1$-$C_6$-alkoxy-" is to be understood as preferably meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentyloxy, iso-pentyloxy, n-hexyloxy group, or an isomer thereof. Particularly, the "$C_1$-$C_6$-alkoxy-" group is a "$C_1$-$C_4$-alkoxy-", a "$C_1$-$C_3$-alkoxy-", a methoxy, ethoxy, or propoxy group, preferably a methoxy, ethoxy or propoxy group. Further preferred is a "$C_1$-$C_2$-alkoxy-" group, particularly a methoxy or ethoxy group.

The term "$C_1$-$C_3$-fluoroalkoxy-" is to be understood as preferably meaning a linear or branched, saturated, monovalent, $C_1$-$C_3$-alkoxy- group, as defined supra, in which one or more of the hydrogen atoms is replaced, identically or differently, by one or more fluoro atoms. Said $C_1$-$C_3$-fluoroalkoxy-group is, for example a 1,1-difluoromethoxy-, a 1,1,1-trifluoromethoxy-, a 2-fluoroethoxy-, a 3-fluoropropoxy-, a 2,2,2-trifluoroethoxy-, a 3,3,3-trifluoropropoxy-, particularly a "$C_1$-$C_2$-fluoroalkoxy-" group.

The term "alkylamino-" is to be understood as preferably meaning an alkylamino group with one linear or branched alkyl group as defined supra. ($C_1$-$C_3$)-alkylamino- for example means a monoalkylamino group with 1, 2 oder 3 carbon atoms, ($C_1$-$C_6$)-alkylamino- with 1, 2, 3, 4, 5 or 6 carbon atoms. The term "alkylamino-" comprises for example methylamino-, ethylamino-, n-propylamino-, iso-propylamino-, tert.-butylamino-, n-pentylamino- or n-hexylamino-.

The term "dialkylamino-" is to be understood as preferably meaning an alkylamino group having two linear or branched alkyl groups as defined supra, which are independent from each other. ($C_1$-$C_3$)-dialkylamino- for example represents a dialkylamino group with two alkyl groups each of them having 1 to 3 carbon atoms per alkyl group. The term "dialkylamino-" comprises for example: N,N-Dimethylamino-, N,N-Diethylamino-, N-Ethyl-N-methylamino-, N-Methyl-N-n-propylamino-, N-Isopropyl-N-n-propylamino-, N-t-Butyl-N-methylamino-, N-Ethyl-N-n-pentylamino- and N-n-Hexyl-N-methylamino-.

The term "cyclic amine" is to be understood as preferably meaning a cyclic amine group. Preferably, a cyclic amine means a saturated, monocyclic group with 4 to 10, preferably 4 to 7 ring atoms of which at least one ring atom is a nitrogen atom. Suitable cyclic amines are especially azetidine, pyrrolidine, piperidine, piperazine, 1-methylpiperazine, morpholine, thiomorpholine, which could be optionally substituted by one or two methyl groups.

The term "halo-$C_1$-$C_3$-alkyl-" is to be understood as preferably meaning a linear or branched, saturated, monovalent hydrocarbon group in which the term "$C_1$-$C_3$-alkyl" is defined supra, and in which one or more hydrogen atoms is replaced by a halogen atom, identically or differently, i.e. one halogen atom being independent from another. Particularly, said halogen atom is fluorine. Preferably, a halo-$C_1$-$C_3$-alkyl- group is a fluoro-$C_1$-$C_3$-alkyl- or a fluoro-$C_1$-$C_2$-alkyl- group, such as for example —$CF_3$, —$CHF_2$, —$CH_2F$, —$CF_2CF_3$, or —$CH_2CF_3$, more preferably it is —$CF_3$.

The term "phenyl-$C_1$-$C_3$-alkyl-" is to be understood as preferably meaning a phenyl group, in which one of the hydrogen atoms is replaced by a $C_1$-$C_3$-alkyl group, as defined supra, that links the phenyl-$C_1$-$C_3$-alkyl-group to the molecule. Particularly, the "phenyl-$C_1$-$C_3$-alkyl-" is a phenyl-$C_1$-$C_2$-alkyl-, preferably it is a benzyl- group.

The term "heteroaryl" is to be understood as preferably meaning a monovalent, aromatic ring system having 5, 6, 7, 8, 9, 10, 11, 12, 13 or 14 ring atoms (a "5- to 14-membered heteroaryl" group), particularly 5 (a "5-membered heteroaryl") or 6 (a "6-membered heteroaryl") or 9 (a "9-membered heteroaryl") or 10 ring atoms (a "10-membered heteroaryl"), and which contains at least one heteroatom which may be identical or different, said heteroatom being such as oxygen, nitrogen or sulfur, and can be monocyclic, bicyclic, or tricyclic, and in addition in each case can be benzo-condensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, or oxepinyl, etc. Preferably, heteroaryl is selected from monocyclic heteroaryl, 5-membered heteroaryl or 6-membered heteroaryl.

The term "5-membered heteroaryl" is understood as preferably meaning a monovalent, aromatic ring system having 5 ring atoms and which contains at least one heteroatom which may be identical or different, said heteroatom being such as oxygen, nitrogen or sulfur. Particularly, "5-membered heteroaryl" is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl.

The term "6-membered heteroaryl" is understood as preferably meaning a monovalent, aromatic ring system having 6 ring atoms and which contains at least one heteroatom which may be identical or different, said heteroatom being such as oxygen, nitrogen or sulfur. Particularly, "6-membered heteroaryl" is selected from pyridyl, pyridazinyl, pyrimidinyl, pyrazinyl, triazinyl.

The term "heteroaryl-$C_1$-$C_3$-alkyl-" is to be understood as preferably meaning a heteroaryl, a 5-membered heteroaryl or a 6-membered heteroaryl group, each as defined supra, in which one of the hydrogen atoms is replaced by a $C_1$-$C_3$-alkyl group, as defined supra, that links the heteroaryl-$C_1$-$C_3$-alkyl- group to the molecule. Particularly, the "heteroaryl-$C_1$-$C_3$-alkyl-" is a heteroaryl-$C_1$-$C_2$-alkyl-, a pyridinyl-$C_1$-$C_3$-alkyl-, a pyridinylmethyl-, a pyridinylethyl-, a pyridinylpropyl-, a pyrimidinyl-$C_1$-$C_3$-alkyl-, a pyrimidinylmethyl-, a pyrimidinylethyl-, a pyrimidinylpropyl-, preferably a pyridinylmethyl- or a pyridinylethyl- or a pyrimidinylethyl- or a pyrimidinylpropyl- group.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene) sulfonyloxy, (4-nitro-benzene) sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

The term "$C_1$-$C_{10}$", as used throughout this text, e.g. in the context of the definition of "$C_1$-$C_{10}$-alkyl" is to be understood as meaning an alkyl group having a finite number of carbon atoms of 1 to 10, i.e. 1, 2, 3, 4, 5, 6, 7, 8, 9 or 10 carbon atoms. It is to be understood further that said term "$C_1$-$C_{10}$" is to be interpreted as any sub-range comprised therein, e.g. $C_1$-$C_{10}$, $C_1$-$C_9$, $C_1$-$C_8$, $C_1$-$C_7$, $C_1$-$C_6$ $C_1$-$C_5$, $C_1$-$C_4$, $C_1$-$C_3$, $C_1$-$C_2$, $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$, $C_9$-$C_{10}$.

Similarly, as used herein, the term "$C_1$-$C_6$", as used throughout this text, e.g. in the context of the definition of "$C_1$-$C_6$-alkyl", "$C_1$-$C_6$-alkoxy" is to be understood as meaning an alkyl group having a finite number of carbon atoms of 1 to 6, i.e. 1, 2, 3, 4, 5 or 6 carbon atoms. It is to be understood further that said term "$C_1$-$C_6$" is to be interpreted as any sub-range comprised therein, e.g. $C_1$-$C_6$ $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, $C_5$-$C_6$.

Similarly, as used herein, the term "$C_1$-$C_3$", as used throughout this text, e.g. in the context of the definition of "$C_1$-$C_3$-alkyl", "$C_1$-$C_3$-alkoxy" or "$C_1$-$C_3$-fluoroalkoxy" is to be understood as meaning an alkyl group having a finite number of carbon atoms of 1 to 3, i.e. 1, 2 or 3 carbon atoms. It is to be understood further that said term "$C_1$-$C_3$" is to be interpreted as any sub-range comprised therein, e.g. $C_1$-$C_3$, $C_1$-$C_2$, $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_3$-$C_5$, $C_3$-$C_4$, $C_4$-$C_6$, $C_4$-$C_5$, $C_5$-$C_6$.

Further, as used herein, the term "$C_3$-$C_7$", as used throughout this text, e.g. in the context of the definition of "$C_3$-$C_7$-cycloalkyl", is to be understood as meaning a cycloalkyl group having a finite number of carbon atoms of 3 to 7, i.e. 3, 4, 5, 6 or 7 carbon atoms, particularly 3, 4, 5 or 6 carbon atoms. It is to be understood further that said term "$C_3$-$C_7$" is to be interpreted as any sub-range comprised therein, e.g. $C_3$-$C_7$, $C_3$-$C_6$, $C_3$-$C_5$, $C_3$-$C_4$, $C_4$-$C_7$, $C_4$-$C_6$, $C_4$-$C_5$, $C_5$-$C_7$, $C_5$-$C_6$, $C_6$-$C_7$.

A symbol ⌇ at a bond denotes the linkage site in the molecule.

As used herein, the term "one or more times", e.g. in the definition of the substituents of the compounds of the general formulae of the present invention, is understood as meaning one, two, three, four or five times, particularly one, two, three or four times, more particularly one, two or three times, even more particularly one or two times.

Where the plural form of the word compounds, salts, hydrates, solvates and the like, is used herein, this is taken to mean also a single compound, salt, isomer, hydrate, solvate or the like.

In another embodiment the present invention concerns compounds of general formula (I), wherein $R^1$ represents a $C_1$-$C_6$-alkyl- or $C_3$-$C_5$-cycloalkyl group, wherein said group is optionally substituted with one substituent selected from the group of hydroxy, $C_1$-$C_3$-alkyl-, $C_1$-$C_3$-alkoxy-, $C_1$-$C_2$-fluoroalkoxy-, —NH$_2$, alkylamino-, dialkylamino-, cyclic amines, —OP(O)(OH)$_2$, —C(O)OH, —C(O)NH$_2$;

$R^2$ represents the group

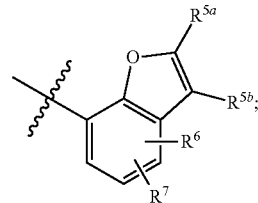

$R^3$ represents a hydrogen atom, a fluoro atom, a chloro atom, $C_1$-$C_3$-alkyl or a fluoro-$C_1$-$C_3$-alkyl-group;

$R^4$ represents a hydrogen atom or a fluoro atom;

$R^{5a}$, $R^{5b}$ represent, independently from each other, a group selected from a hydrogen atom, a fluoro atom, a chloro atom, a bromo atom, cyano, $C_1$-$C_2$-alkyl-, $C_1$-$C_2$-alkoxy-, fluoro-$C_1$-$C_2$-alkyl-, $C_1$-$C_2$-fluoroalkoxy-;

$R^6$, $R^7$ represent, independently from each other, a group selected from a hydrogen atom, a fluoro atom, a chloro atom, a bromo atom, cyano, $C_1$-$C_2$-alkyl-, $C_1$-$C_2$-alkoxy-, fluoro-$C_1$-$C_2$-alkyl-, $C_1$-$C_2$-fluoroalkoxy-;

or their salts, solvates or salts of solvates.

In a preferred embodiment the present invention concerns compounds of general formula (I), wherein $R^1$ represents a $C_1$-$C_6$-alkyl- or $C_3$-$C_5$-cycloalkyl group, wherein said group is optionally substituted with one substituent selected from the group of hydroxy, $C_1$-$C_3$-alkoxy, —NH$_2$, alkylamino-, dialkylamino-, cyclic amines, —OP(O)(OH)$_2$;

$R^2$ represents the group

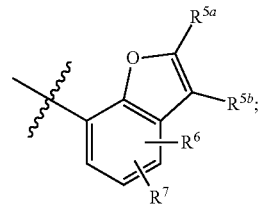

$R^3$ represents a hydrogen atom, a fluoro atom or a chloro atom, a $C_1$-$C_3$-alkyl group or a fluoro-$C_1$-$C_3$-alkyl group;

$R^4$ represents a hydrogen atom or a fluoro atom;

$R^{5a}$, $R^{5b}$ represent, independently from each other, a group selected from a hydrogen atom, a fluoro atom, a chloro atom, a bromo atom, cyano, methyl-, methoxy-, difluoromethyl-, trifluoromethyl-, difluoromethoxy-, trifluoromethoxy-;

$R^6$, $R^7$ represent, independently from each other, a group selected from a hydrogen atom, a fluoro atom and a chloro atom;

or their salts, solvates or salts of solvates.

In another preferred embodiment the present invention concerns compounds of general formula (I), wherein $R^1$ represents a $C_1$-$C_6$-alkyl group, wherein said group is optionally substituted with one substituent, selected from the group of $C_1$-$C_3$-alkoxy, —NH$_2$, alkylamino-, dialkylamino-, and cyclic amines;

$R^2$ represents the group

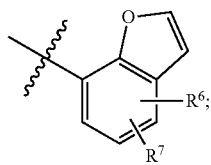

$R^3$ represents a hydrogen atom, a fluoro atom or a methyl- or trifluoromethyl- group;
$R^4$ represents a hydrogen atom or fluoro atom;
$R^6$, $R^7$ represent, independently from each other, a group selected from a hydrogen atom, a fluoro atom and a chloro atom;
or their salts, solvates or salts of solvates.

In a particularly preferred embodiment the present invention concerns compounds of general formula (I), wherein
$R^1$ represents a $C_1$-$C_3$-alkyl group;
$R^2$ represents the group

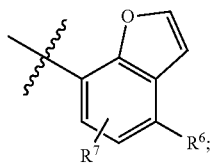

$R^3$ represents a hydrogen atom, a fluoro atom or a methyl- or trifluoromethyl- group;
$R^4$ represents a hydrogen atom;
$R^6$ represents a group selected from hydrogen, a fluoro atom and a chloro atom;
$R^7$ represents hydrogen;
or their salts, solvates or salts of solvates.

In another particularly preferred embodiment the present invention concerns compounds of general formula (I), wherein
$R^1$ represents a methyl group;
$R^2$ represents the group

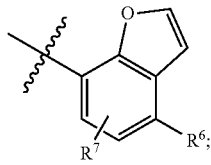

$R^3$ represents a hydrogen atom, a fluoro atom or a methyl- or trifluoromethyl- group;
$R^4$ represents a hydrogen atom;
$R^6$ represents a group selected from hydrogen and a fluoro atom,
$R^7$ represents hydrogen;
or their salts, solvates or salts of solvates.

In another embodiment the invention relates to compounds of formula (I), in which $R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- or heteroaryl-$C_1$-$C_3$-alkyl-,
wherein said group is optionally substituted with one or two or three substituents, identically or differently, selected from the group of hydroxy, cyano, halogen, $C_1$-$C_6$-alkyl-, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines, —OP(O)(OH)$_2$, —C(O)OH, —C(O)NH$_2$.

In another embodiment the invention relates to compounds of formula (I), in which $R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- or heteroaryl-$C_1$-$C_3$-alkyl-,
wherein said group is optionally substituted with one or two or three substituents, identically or differently, selected from the group of hydroxy, $C_1$-$C_3$-alkyl-, fluoro-$C_1$-$C_2$-alkyl-, $C_1$-$C_3$-alkoxy-, $C_1$-$C_2$-fluoroalkoxy-, —$NH_2$, alkylamino-, dialkylamino-, cyclic amines, —OP(O)(OH)$_2$, —C(O)OH, —C(O)NH$_2$.

In another embodiment the invention relates to compounds of formula (I), in which $R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- or heteroaryl-$C_1$-$C_3$-alkyl-,
wherein said group is optionally substituted with one or two or three substituents, identically or differently, selected from the group of hydroxy, $C_1$-$C_3$-alkoxy-, —$NH_2$, alkylamino-, dialkylamino-, cyclic amines, —OP(O)(OH)$_2$.

In another embodiment the invention relates to compounds of formula (I), in which $R^1$ represents a $C_1$-$C_6$-alkyl- or $C_3$-$C_5$-cycloalkyl group,
wherein said group is optionally substituted with one or two or three substituents, identically or differently, selected from the group of hydroxy, $C_1$-$C_3$-alkyl-, fluoro-$C_1$-$C_2$-alkyl-, $C_1$-$C_3$-alkoxy-, $C_1$-$C_2$-fluoroalkoxy-, —$NH_2$, alkylamino-, dialkylamino-, cyclic amines, —OP(O)(OH)$_2$, —C(O)OH, —C(O)NH$_2$.

In a preferred embodiment the present invention concerns compounds of general formula (I), in which $R^1$ represents a $C_1$-$C_6$-alkyl- or $C_3$-$C_5$-cycloalkyl group,
wherein said group is optionally substituted with one substituent selected from the group of hydroxy, $C_1$-$C_3$-alkoxy-, —$NH_2$, alkylamino-, dialkylamino-, cyclic amines, —OP(O)(OH)$_2$.

In another preferred embodiment the present invention concerns compounds of general formula (I), in which $R^1$ represents a $C_1$-$C_6$-alkyl- or $C_3$-$C_5$-cycloalkyl group,
wherein said group is optionally substituted with one substituent selected from the group of $C_1$-$C_3$-alkoxy, —$NH_2$, alkylamino-, dialkylamino-, and cyclic amines.

In another preferred embodiment the present invention concerns compounds of general formula (I), in which $R^1$ represents a $C_1$-$C_6$-alkyl- group,
wherein said group is optionally substituted with one substituent selected from the group of hydroxy, $C_1$-$C_3$-alkoxy-, —$NH_2$, alkylamino-, dialkylamino-, cyclic amines, —OP(O)(OH)$_2$.

In another preferred embodiment the present invention concerns compounds of general formula (I), in which $R^1$ represents a $C_1$-$C_6$-alkyl- group,
wherein said group is optionally substituted with one substituent selected from the group of $C_1$-$C_3$-alkoxy, —$NH_2$, alkylamino-, dialkylamino-, and cyclic amines.

In a particularly preferred embodiment the present invention concerns compounds of general formula (I), in which $R^1$ represents a $C_1$-$C_3$-alkyl- group.

In another particularly preferred embodiment the present invention concerns compounds of general formula (I), in which $R^1$ represents an iso-propyl group.

In another particularly preferred embodiment the present invention concerns compounds of general formula (I), in which $R^1$ represents a n-propyl group.

In another particularly preferred embodiment the present invention concerns compounds of general formula (I), in which $R^1$ represents an ethyl group.

In another particularly preferred embodiment the present invention concerns compounds of general formula (I), in which $R^1$ represents a methyl group.

In another embodiment the invention relates to compounds of formula (I), in which $R^2$ represents a group

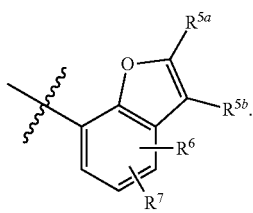

In a preferred embodiment the invention relates to compounds of formula (I), in which $R^2$ represents a group

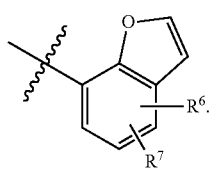

In a particularly preferred embodiment the invention relates to compounds of formula (I), in which $R^2$ represents a group

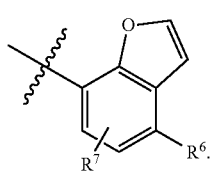

In another particularly preferred embodiment the invention relates to compounds of formula (I), in which $R^2$ represents a group selected from 4-fluoro-1-benzofuran-7-yl- or 1-benzofuran-7-yl-.

In another particularly preferred embodiment the invention relates to compounds of formula (I), in which $R^2$ represents a 4-fluoro-1-benzofuran-7-yl- group.

In another particularly preferred embodiment the invention relates to compounds of formula (I), in which $R^2$ represents a 1-benzofuran-7-yl- group.

In another embodiment the invention relates to compounds of formula (I), in which $R^3$ and $R^4$ represent, independently from each other, a group selected from a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^3$ and $R^4$ represent, independently from each other, a group selected from a hydrogen atom, a fluoro atom, a chloro atom, a bromo atom, cyano, $C_1$-$C_3$-alkyl-, $C_1$-$C_3$-alkoxy-, fluoro-$C_1$-$C_3$-alkyl-, $C_1$-$C_3$-fluoroalkoxy-.

In another embodiment the invention relates to compounds of formula (I), in which $R^3$ and $R^4$ represent, independently from each other, a group selected from a hydrogen atom, a fluoro atom, a chloro atom, a bromo atom, cyano, $C_1$-$C_2$-alkyl-, $C_1$-$C_2$-alkoxy-, fluoro-$C_1$-$C_2$-alkyl-, $C_1$-$C_2$-fluoroalkoxy-.

In another embodiment the invention relates to compounds of formula (I), in which $R^3$ and $R^4$ represent, independently from each other, a group selected from a hydrogen atom, a fluoro atom, a chloro atom, a bromo atom, cyano, methyl-, methoxy-, difluoromethyl-, trifluoromethyl-, difluoromethoxy-, trifluoromethoxy-.

In another embodiment the invention relates to compounds of formula (I), in which $R^3$ and $R^4$ represent, independently from each other, a group selected from a hydrogen atom, a fluoro atom or a chloro atom, a $C_1$-$C_3$-alkyl group or a fluoro-$C_1$-$C_3$-alkyl group.

In a preferred embodiment the invention relates to compounds of formula (I), in which $R^3$ and $R^4$ represent, independently from each other, a group selected from a hydrogen atom, a fluoro atom or a methyl- or trifluoromethyl- group.

In another embodiment the invention relates to compounds of formula (I), in which $R^3$ represents a group selected from a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-, and in which $R^4$ represents a hydrogen atom, a fluoro atom, a chloro atom, a bromo atom or cyano.

In another embodiment the invention relates to compounds of formula (I), in which $R^3$ represents a group selected from a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-, and in which $R^4$ represents a hydrogen atom, a fluoro atom or a chloro atom.

In another embodiment the invention relates to compounds of formula (I), in which $R^3$ represents a group selected from a hydrogen atom, a fluoro atom, a chloro atom, a bromo atom, cyano, $C_1$-$C_2$-alkyl-, $C_1$-$C_2$-alkoxy-, halo-$C_1$-$C_2$-alkyl-, $C_1$-$C_2$-fluoroalkoxy-, and in which $R^4$ represents a hydrogen atom or a fluoro atom.

In a preferred embodiment the invention relates to compounds of formula (I), in which $R^3$ represents a group selected from a hydrogen atom, a fluoro atom or a chloro atom, a $C_1$-$C_3$-alkyl group or a fluoro-$C_1$-$C_3$-alkyl group, and in which $R^4$ represents a hydrogen atom or a fluoro atom.

In another preferred embodiment the invention relates to compounds of formula (I), in which $R^3$ represents a group selected from a hydrogen atom, a fluoro atom or a chloro atom, a $C_1$-$C_3$-alkyl group or a fluoro-$C_1$-$C_3$-alkyl group, and in which $R^4$ represents a hydrogen atom.

In another preferred embodiment the invention relates to compounds of formula (I), in which $R^3$ represents a group selected from a hydrogen atom, a fluoro atom, a chloro atom, a bromo atom, cyano, methyl-, methoxy-, difluoromethyl-, trifluoromethyl-, difluoromethoxy-, trifluoromethoxy-, and in which $R^4$ represents a hydrogen atom or a fluoro atom.

In another preferred embodiment the invention relates to compounds of formula (I), in which $R^3$ represents a group selected from a hydrogen atom, a fluoro atom, a chloro atom, a bromo atom, cyano, methyl-, methoxy-, difluoromethyl-, trifluoromethyl-, difluoromethoxy-, trifluoromethoxy-, and in which $R^4$ represents a hydrogen atom.

In a particularly preferred embodiment the invention relates to compounds of formula (I), in which $R^3$ represents a group selected from a hydrogen atom, a fluoro atom or a methyl- or trifluoromethyl- group, and in which $R^4$ represents a hydrogen atom or a fluoro atom.

In a particularly preferred embodiment the invention relates to compounds of formula (I), in which $R^3$ represents a group selected from a hydrogen atom, a fluoro atom or a methyl- or trifluoromethyl- group, and in which $R^4$ represents a hydrogen atom.

In another embodiment the invention relates to compounds of formula (I), in which $R^3$ represents a group selected from a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^3$ represents a group selected from a hydrogen atom, a fluoro atom, a chloro atom, a bromo atom, cyano, $C_1$-$C_3$-alkyl-, $C_1$-$C_3$-alkoxy-, fluoro-$C_1$-$C_3$-alkyl-, $C_1$-$C_3$-fluoroalkoxy-.

In another embodiment the invention relates to compounds of formula (I), in which $R^3$ represents a group selected from a hydrogen atom, a fluoro atom, a chloro atom, a bromo atom, cyano, $C_1$-$C_2$-alkyl-, $C_1$-$C_2$-alkoxy-, fluoro-$C_1$-$C_2$-alkyl-, $C_1$-$C_2$-fluoroalkoxy-.

In a preferred embodiment the invention relates to compounds of formula (I), in which $R^3$ represents a group selected from a hydrogen atom, a fluoro atom, a chloro atom, a bromo atom, cyano, methyl-, methoxy-, difluoromethyl-, trifluoromethyl-, difluoromethoxy-, trifluoromethoxy-.

In another preferred embodiment the invention relates to compounds of formula (I), in which $R^3$ represents a group selected from a hydrogen atom, a fluoro atom or a chloro atom, a $C_1$-$C_3$-alkyl group or a fluoro-$C_1$-$C_3$-alkyl group.

In another preferred embodiment the invention relates to compounds of formula (I), in which $R^3$ represents a group selected from a hydrogen atom, a fluoro atom or a chloro atom.

In another preferred embodiment the invention relates to compounds of formula (I), in which $R^3$ represents a fluoro atom or a chloro atom.

In another preferred embodiment the invention relates to compounds of formula (I), in which $R^3$ represents a chloro atom.

In another preferred embodiment the invention relates to compounds of formula (I), in which $R^3$ represents a $C_1$-$C_3$-alkyl group or a fluoro-$C_1$-$C_3$-alkyl group.

In another preferred embodiment the invention relates to compounds of formula (I), in which $R^3$ represents a $C_1$-$C_3$-alkyl group.

In another preferred embodiment the invention relates to compounds of formula (I), in which $R^3$ represents a fluoro-$C_1$-$C_3$-alkyl group.

In a particularly preferred embodiment the invention relates to compounds of formula (I), in which $R^3$ represents a hydrogen atom, a fluoro atom or a methyl- or trifluoromethyl- group.

In a particularly preferred embodiment the invention relates to compounds of formula (I), in which $R^3$ represents a hydrogen atom or a fluoro atom.

In a particularly preferred embodiment the invention relates to compounds of formula (I), in which $R^3$ represents a methyl- or trifluoromethyl- group.

In another particularly preferred embodiment the invention relates to compounds of formula (I), in which $R^3$ represents a hydrogen atom.

In another particularly preferred embodiment the invention relates to compounds of formula (I), in which $R^3$ represents a fluoro atom.

In another particularly preferred embodiment the invention relates to compounds of formula (I), in which $R^3$ represents a methyl group.

In another particularly preferred embodiment the invention relates to compounds of formula (I), in which $R^3$ represents a trifluoromethyl- group.

In another embodiment the invention relates to compounds of formula (I), in which $R^4$ represents a group selected from a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^4$ represents a group selected from a hydrogen atom, a fluoro atom, a chloro atom, a bromo atom, cyano, methyl-, methoxy-, difluoromethyl-, trifluoromethyl-, difluoromethoxy-, trifluoromethoxy-.

In another embodiment the invention relates to compounds of formula (I), in which $R^4$ represents a hydrogen atom, a fluoro atom, a chloro atom, a bromo atom or cyano.

In another embodiment the invention relates to compounds of formula (I), in which $R^4$ represents a hydrogen atom, a fluoro atom, a chloro atom or a bromo atom.

In another embodiment the invention relates to compounds of formula (I), in which $R^4$ represents a hydrogen atom, a fluoro atom or a chloro atom.

In a preferred embodiment the invention relates to compounds of formula (I), in which $R^4$ represents a hydrogen atom or a fluoro atom.

In another preferred embodiment the invention relates to compounds of formula (I), in which $R^4$ represents a hydrogen atom.

In another preferred embodiment the invention relates to compounds of formula (I), in which $R^4$ represents a fluoro atom.

In another embodiment the invention relates to compounds of formula (I), in which $R^{5a}$ and $R^{5b}$ represent, independently from each other, a group selected from a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^{5a}$ and $R^{5b}$ represent, independently from each other, a group selected from a hydrogen atom, a fluoro atom, a chloro atom, a bromo atom, cyano, $C_1$-$C_3$-alkyl-, $C_1$-$C_3$-alkoxy-, fluoro-$C_1$-$C_3$-alkyl-, $C_1$-$C_3$-fluoroalkoxy-.

In another embodiment the invention relates to compounds of formula (I), in which $R^{5a}$ and $R^{5b}$ represent, independently from each other, a hydrogen atom, a fluoro atom, a chloro atom, a bromo atom, cyano, methyl-, methoxy-, difluoromethyl-, trifluoromethyl-, difluoromethoxy-, trifluoromethoxy-.

In another embodiment the invention relates to compounds of formula (I), in which $R^{5a}$ represents a hydrogen atom, a fluoro atom, a chloro atom, a bromo atom, cyano, methyl-, methoxy-, difluoromethyl-, trifluoromethyl-, difluoromethoxy-, trifluoromethoxy-, and $R^{5b}$ represents a hydrogen atom or a fluoro atom.

In another embodiment the invention relates to compounds of formula (I), in which $R^{5a}$ represents a hydrogen atom or a fluoro atom, and $R^{5b}$ represents a hydrogen atom, a fluoro atom, a chloro atom, a bromo atom, cyano, methyl-, methoxy-, difluoromethyl-, trifluoromethyl-, difluoromethoxy-, trifluoromethoxy-.

In another embodiment the invention relates to compounds of formula (I), in which $R^{5a}$ represents a hydrogen atom or a fluoro atom, and $R^{5b}$ represents a hydrogen atom, a fluoro atom, a chloro atom, methyl-, methoxy or trifluoromethyl-.

In another embodiment the invention relates to compounds of formula (I), in which $R^{5a}$ represents a hydrogen atom, a fluoro atom, a chloro atom, methyl-, methoxy or trifluoromethyl-, and $R^{5b}$ represents a hydrogen atom or a fluoro atom.

In another embodiment the invention relates to compounds of formula (I), in which $R^{5a}$ represents a hydrogen atom, and $R^{5b}$ represents a hydrogen atom, a fluoro atom, a chloro atom, methyl-, methoxy or trifluoromethyl-.

In another embodiment the invention relates to compounds of formula (I), in which $R^{5a}$ represents a hydrogen atom, a fluoro atom, a chloro atom, methyl-, methoxy or trifluoromethyl-, and $R^{5b}$ represents a hydrogen atom.

In another embodiment the invention relates to compounds of formula (I), in which $R^{5a}$ represents a hydrogen atom, and $R^{5b}$ represents a hydrogen atom, a fluoro atom or methyl-.

In another embodiment the invention relates to compounds of formula (I), in which $R^{5a}$ represents a hydrogen atom, a fluoro atom or methyl-, and $R^{5b}$ represents a hydrogen atom.

In another embodiment the invention relates to compounds of formula (I), in which $R^{5a}$ represents a hydrogen atom, and $R^{5b}$ represents a hydrogen atom or a fluoro atom.

In another embodiment the invention relates to compounds of formula (I), in which $R^{5a}$ represents a hydrogen atom or a fluoro atom, and $R^{5b}$ represents a hydrogen atom.

In another embodiment the invention relates to compounds of formula (I), in which $R^{5a}$ and $R^{5b}$ represent a hydrogen atom.

In another embodiment the invention relates to compounds of formula (I), in which $R^6$ and $R^7$ represent, independently from each other, a group selected from a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^6$ and $R^7$ represent, independently from each other, a group selected from hydrogen, a fluoro atom, a chloro atom, a bromo atom, cyano, $C_1$-$C_3$-alkyl-, $C_1$-$C_3$-alkoxy-, fluoro-$C_1$-$C_3$-alkyl-, $C_1$-$C_3$-fluoroalkoxy-.

In another embodiment the invention relates to compounds of formula (I), in which $R^6$ and $R^7$ represent, independently from each other, a group selected from hydrogen, a fluoro atom, a chloro atom, a bromo atom, cyano, $C_1$-$C_2$-alkyl-, $C_1$-$C_2$-alkoxy-, fluoro-$C_1$-$C_2$-alkyl-, $C_1$-$C_2$-fluoroalkoxy-.

In another embodiment the invention relates to compounds of formula (I), in which $R^6$ and $R^7$ represent, independently from each other, hydrogen, a fluoro atom, a chloro atom, a bromo atom, cyano, methyl-, methoxy-, difluoromethyl-, trifluoromethyl-, difluoromethoxy-, trifluoromethoxy-.

In another embodiment the invention relates to compounds of formula (I), in which $R^6$ and $R^7$ represent, independently from each other, a hydrogen atom, a fluoro atom, a chloro atom, a bromo atom, cyano or methyl-.

In another embodiment the invention relates to compounds of formula (I), in which $R^6$ and $R^7$ represent, independently from each other, a hydrogen atom, a fluoro atom, a chloro atom, a bromo atom or cyano.

In a preferred embodiment the invention relates to compounds of formula (I), in which $R^6$ and $R^7$ represent, independently from each other, a hydrogen atom, a fluoro atom or a chloro atom.

In another preferred embodiment the invention relates to compounds of formula (I), in which $R^6$ and $R^7$ represent, independently from each other, a hydrogen atom or a fluoro atom.

In another embodiment the invention relates to compounds of formula (I), in which $R^6$ represents a group selected from a hydrogen atom, a fluoro atom, a chloro atom, a bromo atom, cyano, $C_1$-$C_2$-alkyl-, $C_1$-$C_2$-alkoxy-, fluoro-$C_1$-$C_2$-alkyl-, $C_1$-$C_2$-fluoroalkoxy-, and $R^7$ represents a hydrogen atom, a fluoro atom or a chloro atom.

In another embodiment the invention relates to compounds of formula (I), in which $R^6$ represents a hydrogen atom, a fluoro atom or a chloro atom, and $R^7$ represents a group selected from a hydrogen atom, a fluoro atom or a chloro atom, a bromo atom, cyano, $C_1$-$C_2$-alkyl-, $C_1$-$C_2$-alkoxy-, fluoro-$C_1$-$C_2$-alkyl-, $C_1$-$C_2$-fluoroalkoxy-.

In another embodiment the invention relates to compounds of formula (I), in which $R^6$ represents a hydrogen atom, a fluoro atom, a chloro atom, a bromo atom, cyano, methyl-, methoxy-, difluoromethyl-, trifluoromethyl-, difluoromethoxy-, trifluoromethoxy-, and $R^7$ represents a hydrogen atom, a fluoro atom or a chloro atom.

In another embodiment the invention relates to compounds of formula (I), in which $R^6$ represents a hydrogen atom, a fluoro atom or a chloro atom, and $R^7$ represents a hydrogen atom, a fluoro atom, a chloro atom, a bromo atom, cyano, methyl-, methoxy-, difluoromethyl-, trifluoromethyl-, difluoromethoxy-, trifluoromethoxy-.

In another embodiment the invention relates to compounds of formula (I), in which $R^6$ represents a hydrogen atom, a fluoro atom, a chloro atom, a bromo atom, cyano or methyl-, and $R^7$ represents a hydrogen atom or a fluoro atom.

In another embodiment the invention relates to compounds of formula (I), in which $R^6$ represents a hydrogen atom or a fluoro atom, a chloro atom, and $R^7$ represents a hydrogen atom, a fluoro atom, a chloro atom a bromo atom, cyano or methyl-.

In another embodiment the invention relates to compounds of formula (I), in which $R^6$ represents a hydrogen atom, a fluoro atom, a chloro atom, a bromo atom or cyano, and $R^7$ represents a hydrogen atom or a fluoro atom.

In another embodiment the invention relates to compounds of formula (I), in which $R^6$ represents a hydrogen atom or a fluoro atom, and $R^7$ represents a hydrogen atom, a fluoro atom, a chloro atom a bromo atom or cyano.

In a preferred embodiment the invention relates to compounds of formula (I), in which $R^6$ represents a hydrogen atom, a fluoro atom or a chloro atom, and $R^7$ represents a hydrogen atom or a fluoro atom.

In another preferred embodiment the invention relates to compounds of formula (I), in which $R^6$ represents a hydrogen atom or a fluoro atom, and $R^7$ represents a hydrogen atom, a fluoro atom or a chloro atom.

In another preferred embodiment the invention relates to compounds of formula (I), in which $R^6$ represents a hydrogen atom or a fluoro atom, and $R^7$ represents a hydrogen atom.

In another preferred embodiment the invention relates to compounds of formula (I), in which $R^6$ represents a hydrogen atom, and $R^7$ represents a hydrogen atom or a fluoro atom.

In another preferred embodiment the invention relates to compounds of formula (I), in which $R^6$ represents hydrogen, para-fluoro, or para-chloro, whereby para refers to the point of attachment of $R^2$ to the rest of the molecule, and in which $R^7$ represents a hydrogen atom.

In another preferred embodiment the invention relates to compounds of formula (I), in which $R^6$ represents para-fluoro, whereby para refers to the point of attachment of $R^2$ to the rest of the molecule, and in which $R^7$ represents a hydrogen atom.

In another preferred embodiment the invention relates to compounds of formula (I), in which $R^6$ represents para-fluoro, whereby para refers to the point of attachment of $R^2$ to the rest of the molecule.

In another preferred embodiment the invention relates to compounds of formula (I), in which $R^6$ and $R^7$ represent a hydrogen atom.

In another preferred embodiment the invention relates to compounds of formula (I), in which $R^6$ and $R^7$ represent a fluoro atom.

In another embodiment the invention relates to compounds of formula (I), in which $R^6$ represents a group selected from a hydrogen atom, a fluoro atom, a chloro atom, a bromo atom, cyano, methyl-, methoxy-, difluoromethyl-, trifluoromethyl-, difluoromethoxy-, trifluoromethoxy-.

In another embodiment the invention relates to compounds of formula (I), in which $R^6$ represents a hydrogen atom, a fluoro atom, a chloro atom, a bromo atom or cyano.

In another embodiment the invention relates to compounds of formula (I), in which $R^6$ represents a hydrogen atom, a fluoro atom, a chloro atom or a bromo atom.

In another embodiment the invention relates to compounds of formula (I), in which $R^6$ represents a hydrogen atom, a fluoro atom or a chloro atom.

In a preferred embodiment the invention relates to compounds of formula (I), in which $R^6$ represents a hydrogen atom or a fluoro atom.

In another preferred embodiment the invention relates to compounds of formula (I), in which $R^6$ represents a hydrogen atom.

In another preferred embodiment the invention relates to compounds of formula (I), in which $R^6$ represents a fluoro atom.

In another embodiment the invention relates to compounds of formula (I), in which $R^7$ represents a group selected from a hydrogen atom, a fluoro atom, a chloro atom, a bromo atom, cyano, methyl-, methoxy-, difluoromethyl-, trifluoromethyl-, difluoromethoxy-, trifluoromethoxy-.

In another embodiment the invention relates to compounds of formula (I), in which $R^7$ represents a hydrogen atom, a fluoro atom, a chloro atom, a bromo atom or cyano.

In another embodiment the invention relates to compounds of formula (I), in which $R^7$ represents a hydrogen atom, a fluoro atom, a chloro atom or a bromo atom.

In another embodiment the invention relates to compounds of formula (I), in which $R^7$ represents a hydrogen atom, a fluoro atom or a chloro atom.

In a preferred embodiment the invention relates to compounds of formula (I), in which $R^7$ represents a hydrogen atom or a fluoro atom.

In another preferred embodiment the invention relates to compounds of formula (I), in which $R^7$ represents a hydrogen atom.

In another preferred embodiment the invention relates to compounds of formula (I), in which $R^7$ represents a fluoro atom.

It is to be understood that the present invention relates to any sub-combination within any embodiment of the present invention of compounds of formula (I), supra.

More particularly still, the present invention covers compounds of formula (I) which are disclosed in the Example section of this text, infra.

Very specially preferred are combinations of two or more of the abovementioned preferred embodiments.

In particular, preferred subjects of the present invention are the compounds:
5-Fluoro-4-(4-fluoro-1-benzofuran-7-yl)-N-{4-[(methylsulfonyl)methyl]pyridin-2-yl}pyridin-2-amine,
5-Fluoro-4-(4-fluoro-1-benzofuran-7-yl)-N-{6-fluoro-4-[(methylsulfonyl)methyl]pyridin-2-yl}pyridin-2-amine,
5-Fluoro-4-(4-fluoro-1-benzofuran-7-yl)-N-{6-methyl-4-[(methylsulfonyl)methyl]pyridin-2-yl}pyridin-2-amine,
5-Fluoro-4-(4-fluoro-1-benzofuran-7-yl)-N-{4-[(methylsulfonyl)methyl]-6-(trifluoromethyl)pyridin-2-yl}pyridin-2-amine,
4-(1-Benzofuran-7-yl)-5-fluoro-N-{4-[(methylsulfonyl)methyl]pyridin-2-yl}pyridin-2-amine,
or its salts, solvates or salts of solvates.

The abovementioned definitions of radicals which have been detailed in general terms or in preferred ranges also apply to the end products of the formula (I) and, analogously, to the starting materials or intermediates required in each case for the preparation.

The invention furthermore relates to a method for the preparation of the compounds of formula (I) according to the invention, in which method a compound of formula (3)

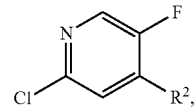

in which $R^2$ is as defined for the compound of general formula (I), is reacted with a compound of formula (9),

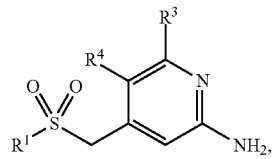

in which $R^1$, $R^3$ and $R^4$ are as defined for the compound of general formula (I), in a Palladium-catalysed C—N cross-coupling reaction,
thus providing a compound of general formula (I) according to the present invention, and in which method the resulting compound of formula (I) is optionally, if appropriate, reacted with the corresponding (i) solvents and/or (ii) bases or acids to the solvates, salts and/or solvates of the salts of the compounds of formula (I).

The compounds according to the invention show a valuable pharmacological and pharmacokinetic spectrum of action which could not have been predicted.

They are therefore suitable for use as medicaments for the treatment and/or prophylaxis of disorders in humans and animals.

Within the scope of the present invention, the term "treatment" includes prophylaxis.

The pharmaceutical activity of the compounds according to the invention can be explained by their action as inhibitors of CDK9. Thus, the compounds according to the general formula (I) as well as pharmaceutically acceptable salts thereof are used as inhibitors for CDK9.

Furthermore, the compounds according to the invention show a particularly high potency (demonstrated by a low $IC_{50}$ value in the CDK9/CycT1 assay) for inhibiting CDK9 activity.

In context of the present invention, the $IC_{50}$ value with respect to CDK9 can be determined by the methods described in the method section below. Preferably, it is determined according to Method 1a. ("CDK9/CycT1 kinase assay") described in the Materials and Method section below.

Surprisingly it turned out that the compounds according to the general formula (I) as well as pharmaceutically acceptable salts thereof selectively inhibit CDK9 in comparison to other cyclin-dependent protein kinases, preferably in comparison to CDK2. Thus, the compounds according to the general formula (I) as well as pharmaceutically acceptable salts thereof are preferably used as selective inhibitors for CDK9.

Compounds of the present invention according to general formula (I) show a significantly stronger CDK9 than CDK2 inhibition.

In context of the present invention, the $IC_{50}$ value with respect to CDK2 can be determined by the methods described in the method section below. Preferably, it is determined according to Method 2. ("CDK2/CycE kinase assay") described in the Materials and Method section below.

Further, as compared to the CDK9 inhibitors described in the prior art, preferred compounds of the present invention according to general formula (I) show a surprisingly high potency for inhibiting CDK9 activity at high ATP concentrations, which is demonstrated by their low $IC_{50}$ value in the CDK9/CycT1 high ATP kinase assay. Thus, these compounds have a lower probability to be competed out of the ATP-binding pocket of CDK9/CycT1 kinase due to the high intracellular ATP concentration (R. Copeland et al., Nature Reviews Drug Discovery 2006, 5, 730-739). According to this property the compounds of the present invention are particularly able to inhibit CDK9/CycT1 within cells for a longer period of time as compared to classical ATP competitive kinase inhibitors. This increases the anti-tumor cell efficacy at pharmacokinetic clearance-mediated declining serum concentrations of the inhibitor after dosing of a patient or an animal.

In context of the present invention, the $IC_{50}$ value with respect to CDK9 at high ATP concentrations can be determined by the methods described in the method section below. Preferably, it is determined according to Method 1b ("CDK9/CycT1 high ATP kinase assay") as described in the Materials and Method section below.

Further, preferred compounds of the present invention according to formula (I) show an improved anti-proliferative activity in tumor cell lines such as HeLa, HeLa-MaTu-ADR, NCI-H460, DU145, Caco-2, B16F10 or A2780, compared to the CDK9 inhibitors described in the prior art. In context of the present invention, the anti-proliferative activity in tumor cell lines such as HeLa, HeLa-MaTu-ADR, NCI-H460, DU145, Caco-2, B16F10 or A2780, is preferably determined according to Method 3. ("Proliferation Assay") as described in the Materials and Method section below.

A further subject matter of the present invention is the use of the compounds of general formula (I) according to the invention for the treatment and/or prophylaxis of disorders, preferably of disorders relating to or mediated by CDK9 activity, in particular of hyper-proliferative disorders, virally induced infectious diseases and/or of cardiovascular diseases, more preferably of hyper-proliferative disorders.

The compounds of the present invention may be used to inhibit the activity or expression of CDK9. Therefore, the compounds of formula (I) are expected to be valuable as therapeutic agents. Accordingly, in another embodiment, the present invention provides a method of treating disorders relating to or mediated by CDK9 activity in a patient in need of such treatment, comprising administering to the patient an effective amount of a compound of formula (I) as defined above. In certain embodiments, the disorders relating to CDK9 activity are hyper-proliferative disorders, virally induced infectious diseases and/or of cardiovascular diseases, more preferably hyper-proliferative disorders, particularly cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or a disorder associated with reduced or insufficient programmed cell death (apoptosis) or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "disorders relating to or mediated by CDK9" shall include diseases associated with or implicating CDK9 activity, for example the hyperactivity of CDK9, and conditions that accompany with these diseases. Examples of "disorders relating to or mediated by CDK9" include disorders resulting from increased CDK9 activity due to mutations in genes regulating CDK9 activity such as LARP7, HEXIM1/2 or 7sk snRNA, or disorders resulting from increased CDK9 activity due to activation of the CDK9/cyclinT/RNApolymerase II complex by viral proteins such as HIV-TAT or HTLV-TAX or disorders resulting from increased CDK9 activity due to activation of mitogenic signaling pathways.

The term "hyperactivity of CDK9" refers to increased enzymatic activity of CDK9 as compared to normal non-diseased cells, or it refers to increased CDK9 activity leading to unwanted cell proliferation, or to reduced or insufficient programmed cell death (apoptosis), or mutations leading to constitutive activation of CDK9.

The term "hyper-proliferative disorder" includes disorders involving the undesired or uncontrolled proliferation of a cell and it includes disorders involving reduced or insufficient programmed cell death (apoptosis). The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, hydrate or solvate thereof which is effective to treat or prevent the disorder.

Hyper-proliferative disorders in the context of this invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ, and canine or feline mammary carcinoma.

Examples of cancers of the respiratory tract include, but are not limited to small-cell and non-small-cell lung carcinoma, as well as bronchial adenoma, pleuropulmonary blastoma, and mesothelioma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers. Anal gland adenocarcinomas, mast cell tumors.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer. mast cell tumors.

Head-and-neck cancers include, but are not limited to laryngeal, hypopharyngeal, nasopharyngeal, oropharyngeal cancer, lip and oral cavity cancer, and squamous cell cancer. Oral melanoma.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma. Malignant histiocytosis, fibrosarcoma, hemangiosarcoma, hemangiopericytoma, leiomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present invention include lung fibrosis, atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syn-dromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with subepidermal blister formation, including bullous pemphigoid, erythema multiforme and dermatitis herpetiformis.

The compounds of the present invention may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering pharmaceutical compositions of the present invention.

In a further aspect of the present invention, the compounds according to the invention are used in a method for preventing and/or treating infectious diseases, in particular virally induced infectious diseases. The virally induced infectious diseases, including opportunistic diseases, are caused by retroviruses, hepadnaviruses, herpesviruses, flaviviridae, and/or adenoviruses. In a further preferred embodiment of this method, the retroviruses are selected from lentiviruses or oncoretroviruses, wherein the lentivirus is selected from the group comprising: HIV-1, HIV-2, FIV, BIV, SIVs, SHIV, CAEV, VMV or EIAV, preferably HIV-1 or HIV-2 and wherein the oncoretrovirus is selected from the group of: HTLV-I, HTLV-II or BLV. In a further preferred embodiment of this method, the hepadnavirus is selected from HBV, GSHV or WHV, preferably HBV, the herpesivirus is selected from the group comprising: HSV I, HSV II, EBV, VZV, HCMV or HHV 8, preferably HCMV and the flaviviridae is selected from HCV, West nile or Yellow Fever.

The compounds according to general formula (I) are also useful for prophylaxis and/or treatment of cardiovascular diseases such as cardiac hypertrophy, adult congenital heart disease, aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive cardiomyopathy, hypertrophic cardiomyopathy, restrictive cardiomyopathy, cardiovascular disease prevention, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, restenosis, Sneddon syndrome, stenosis, superior vena cava syndrome, syndrome X, tachycardia, Takayasu's arteritis, hereditary hemorrhagic telangiectasia, telangiectasis, temporal arteritis, tetralogy of fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Preferred are cardiac hypertrophy, adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis.

A further subject matter of the present invention is the use of the compounds of general formula (I) according to the invention as a medicament.

A further subject matter of the present invention is the use of the compounds of general formula (I) according to the invention for the treatment and/or prophylaxis of disorders, in particular of the disorders mentioned above.

A preferred subject matter of the present invention is the use of the compounds of general formula (I) according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas or ovarian carcinomas.

A further subject matter of the present invention are the compounds according to the invention for the use as a medicament.

A further subject matter of the present invention are the compounds according to the invention for the treatment and/or prophylaxis of the disorders mentioned above.

A preferred subject matter of the present invention are the compounds according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas or ovarian carcinomas.

A further subject matter of the present invention are the compounds according to the invention for the use in a method for the treatment and/or prophylaxis of the disorders mentioned above.

A preferred subject matter of the present invention are the compounds according to the invention for the use in a method of treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas or ovarian carcinomas.

A further subject matter of the present invention is the use of the compounds according to the invention in the manufacture of a medicament for the treatment and/or prophylaxis of disorders, in particular the disorders mentioned above.

A preferred subject matter of the present invention is the use of the compounds according to the invention in the manufacture of a medicament for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas or ovarian carcinomas.

A further subject matter of the present invention is a method for the treatment and/or prophylaxis of disorders, in particular the disorders mentioned above, using an effective amount of the compounds according to the invention.

A preferred subject matter of the present invention is a method for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas or ovarian carcinomas using an effective amount of the compounds according to the invention.

Another aspect of the present invention relates to pharmaceutical combinations comprising a compound of general formula (I) according to the invention in combination with at least one or more further active ingredients.

As used herein the term "pharmaceutical combination" refers to a combination of at least one compound of general formula (I) according to the invention as active ingredient together with at least one other active ingredient with or without further ingredients, carrier, diluents and/or solvents.

Another aspect of the present invention relates to pharmaceutical compositions comprising a compound of general formula (I) according to the invention in combination with an inert, nontoxic, pharmaceutically suitable adjuvant.

As used herein the term "pharmaceutical composition" refers to a galenic formulation of at least one pharmaceutically active agent together with at least one further ingredient, carrier, diluent and/or solvent.

Another aspect of the present invention relates to the use of the pharmaceutical combinations and/or the pharmaceutical compositions according to the invention for the treatment and/or prophylaxis of disorders, in particular of the disorders mentioned above.

Another aspect of the present invention relates to the use of the pharmaceutical combinations and/or the pharmaceutical compositions according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas or ovarian carcinomas.

Another aspect of the present invention relates to pharmaceutical combinations and/or the pharmaceutical compositions according to the invention for the treatment and/or prophylaxis of disorders, in particular of the disorders mentioned above.

Another aspect of the present invention relates to pharmaceutical combinations and/or the pharmaceutical compositions according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas or ovarian carcinomas.

Compounds of formula (I) may be administered as the sole pharmaceutical agent or in combination with one or more additional therapeutic agents where the combination causes no unacceptable adverse effects. This pharmaceutical combination includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

- Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, and mitolactol; platinum-coordinated alkylating compounds include, but are not limited to, cisplatin, carboplatin, eptaplatin, lobaplatin, nedaplatin, oxaliplatin, and satraplatin;
- Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfite, disodium premetrexed, pentostatin, pelitrexol, raltitrexed, triapine, trimetrexate, vidarabine, vincristine, and vinorelbine;
- Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and episteride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;
- Plant-derived anti-tumor substances include, e.g., those selected from mitotic inhibitors, for example epothilones such as sagopilone, ixabepilone and epothilone B, vinblastine, vinflunine, docetaxel, and paclitaxel;
- Cytotoxic topoisomerase inhibiting agents include, but are not limited to, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof;
- Immunologicals include interferons such as interferon alpha, interferon alpha-2a, interferon alpha-2b, interferon beta, interferon gamma-1a and interferon gamma-n1, and other immune enhancing agents such as L19-IL2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonermin, tecleukin, thymalasin, tositumomab, Vimlizin, epratuzumab, mitumomab, oregovomab, pemtumomab, and Provenge; Merial melanoma vaccine
- Biological response modifiers are agents that modify defense mechanisms of living organisms or biological responses such as survival, growth or differentiation of tissue cells to direct them to have anti-tumor activity; such agents include, e.g., krestin, lentinan, sizofiran, picibanil, ProMune, and ubenimex;
- Anti-angiogenic compounds include, but are not limited to, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin;
- Antibodies include, but are not limited to, trastuzumab, cetuximab, bevacizumab, rituximab, ticilimumab, ipilimumab, lumiliximab, catumaxomab, atacicept, oregovomab, and alemtuzumab;
- VEGF inhibitors such as, e.g., sorafenib, DAST, bevacizumab, sunitinib, recentin, axitinib, aflibercept, telatinib, brivanib alaninate, vatalanib, pazopanib, and ranibizumab; Palladia
- EGFR (HER1) inhibitors such as, e.g., cetuximab, panitumumab, vectibix, gefitinib, erlotinib, and Zactima;
- HER2 inhibitors such as, e.g., lapatinib, tratuzumab, and pertuzumab;
- mTOR inhibitors such as, e.g., temsirolimus, sirolimus/Rapamycin, and everolimus;
- c-Met inhibitors;
- PI3K and AKT inhibitors;
- CDK inhibitors such as roscovitine and flavopiridol;
- Spindle assembly checkpoints inhibitors and targeted anti-mitotic agents such as PLK inhibitors, Aurora inhibitors (e.g. Hesperadin), checkpoint kinase inhibitors, and KSP inhibitors;
- HDAC inhibitors such as, e.g., panobinostat, vorinostat, MS275, belinostat, and LBH589;
- HSP90 and HSP70 inhibitors;
- Proteasome inhibitors such as bortezomib and carfilzomib;
- Serine/threonine kinase inhibitors including MEK inhibitors (such as e.g. RDEA 119) and Raf inhibitors such as sorafenib;
- Farnesyl transferase inhibitors such as, e.g., tipifarnib;
- Tyrosine kinase inhibitors including, e.g., dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors; Palladia, masitinib
- Vitamin D receptor agonists;
- Bcl-2 protein inhibitors such as obatoclax, oblimersen sodium, and gossypol;
- Cluster of differentiation 20 receptor antagonists such as, e.g., rituximab;
- Ribonucleotide reductase inhibitors such as, e.g., gemcitabine;

Tumor necrosis apoptosis inducing ligand receptor 1 agonists such as, e.g., mapatumumab;
5-Hydroxytryptamine receptor antagonists such as, e.g., rEV598, xaliprode, palonosetron hydrochloride, granisetron, Zindol, and AB-1001;
Integrin inhibitors including alpha5-beta1 integrin inhibitors such as, e.g., E7820, JSM 6425, volociximab, and endostatin;
Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;
Aromatase inhibitors such as, e.g., anastrozole, letrozole, testolactone, exemestane, amino-glutethimide, and formestane;
Matrix metalloproteinase inhibitors;
Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarbazine, dacarbazine, hydroxycarbamide, pegaspargase, pentostatin, tazaroten, velcade, gallium nitrate, canfosfamide, darinaparsin, and tretinoin.

The compounds of the present invention may also be employed in cancer treatment in conjunction with radiation therapy and/or surgical intervention.

Generally, the use of cytotoxic and/or cytostatic agents in combination with a compound or composition of the present invention will serve to:
(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Furthermore, the compounds of formula (I) may be utilized, as such or in compositions, in research and diagnostics, or as analytical reference standards, and the like, which are well known in the art.

The compounds according to the invention can act systemically and/or locally. For this purpose, they can be administered in a suitable way, such as, for example, by the oral, parenteral, pulmonal, nasal, sublingual, lingual, buccal, rectal, dermal, transdermal, conjunctival or otic route, or as an implant or stent.

For these administration routes, it is possible to administer the compounds according to the invention in suitable application forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (coated or uncoated, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneously, percutaneously or intraperitoneally). Administration forms suitable for parenteral administration are, inter alia, preparations for injection and infusion in the form of solutions, suspensions, emulsions, lyophilizates or sterile powders.

Examples suitable for the other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems (such as plasters, for example), milk, pastes, foams, dusting powders, implants or stents.

The compounds according to the invention can be converted into the stated administration forms. This can take place in a manner known per se by mixing with inert, nontoxic, pharmaceutically suitable adjuvants. These adjuvants include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

The present invention furthermore provides medicaments comprising at least one compound according to the invention, usually together with one or more inert, nontoxic, pharmaceutically suitable adjuvants, and their use for the purposes mentioned above.

When the compounds of the present invention are administered as pharmaceuticals, to humans or animals, they can be given per se or as a pharmaceutical composition containing, for example, 0.1% to 99.5% (more preferably 0.5% to 90%) of active ingredient in combination with one or more inert, nontoxic, pharmaceutically suitable adjuvants.

Regardless of the route of administration selected, the compounds of the invention of general formula (I) and/or the pharmaceutical composition of the present invention are formulated into pharmaceutically acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient without being toxic to the patient.

Materials and Methods:

The percentage data in the following tests and examples are percentages by weight unless otherwise indicated; parts are parts by weight. Solvent ratios, dilution ratios and concentration data of liquid/liquid solutions are in each case based on volume.

Examples were tested in selected biological assays one or more times. When tested more than once, data are reported as either average values or as median values, wherein
- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro pharmacological properties of the compounds can be determined according to the following assays and methods.

1a. CDK9/CycT1 Kinase Assay:

CDK9/CycT1-inhibitory activity of compounds of the present invention was quantified employing the CDK9/CycT1 TR-FRET assay as described in the following paragraphs:

Recombinant full-length His-tagged human CDK9 and CycT1, expressed in insect cells and purified by Ni-NTA affinity chromatography, were purchased from Invitrogen (Cat. No PV4131). As substrate for the kinase reaction biotinylated peptide biotin-Ttds-YISPLKSPYKISEG (C-terminus in amid form) was used which can be purchased e.g. form the company JERINI Peptide Technologies (Berlin, Germany). For the assay 50 nl of a 100 fold concentrated solution of the test compound in DMSO was pipetted into a black low volume 384 well microtiter plate (Greiner Bio-One, Frickenhausen, Germany), 2 µl of a solution of CDK9/CycT1 in aqueous assay buffer [50 mM Tris/HCl pH 8.0, 10 mM MgCl$_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 1 µg/mL. The reaction was stopped by the addition of 5 µl of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM. 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and IC$_{50}$ values were calculated by a 4 parameter fit using an inhouse software.

1b. CDK9/CycT1 High ATP Kinase Assay

CDK9/CycT1-inhibitory activity of compounds of the present invention at a high ATP concentration after preincubation of enzyme and test compounds was quantified employing the CDK9/CycT1 TR-FRET assay as described in the following paragraphs.

Recombinant full-length His-tagged human CDK9 and CycT1, expressed in insect cells and purified by Ni-NTA affinity chromatography, were purchase from Invitrogen (Cat. No PV4131). As substrate for the kinase reaction biotinylated peptide biotin-Ttds-YISPLKSPYKISEG (C-terminus in amid form) was used which can be purchased e.g. form the company JERINI peptide technologies (Berlin, Germany). For the assay 50 nl of a 100 fold concentrated solution of the test compound in DMSO was pipetted into a black low volume 384 well microtiter plate (Greiner Bio-One, Frickenhausen, Germany), 2 µl of a solution of CDK9/CycT1 in aqueous assay buffer [50 mM Tris/HCl pH 8.0, 10 mM MgCl$_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 3.3 mM=>final conc. in the 5 µl assay volume is 2 mM) and substrate (1.67 µM=>final conc. in the 5 µl assay volume is 1 µM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 0.5 µg/mL. The reaction was stopped by the addition of 5 µl of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.1 nM (20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

2a. CDK2/CycE Kinase Assay:

CDK2/CycE-inhibitory activity of compounds of the present invention was quantified employing the CDK2/CycE TR-FRET assay as described in the following paragraphs:

Recombinant fusion proteins of GST and human CDK2 and of GST and human CycE, expressed in insect cells (Sf9) and purified by Glutathion-Sepharose affinity chromatography, were purchased from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI Peptide Technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 μl of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 μl of a solution of adenosine-tri-phosphate (ATP, 16.7 μM=>final conc. in the 5 μl assay volume is 10 μM) and substrate (1.25 μM=>final conc. in the 5 μl assay volume is 0.75 μM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 130 ng/mL. The reaction was stopped by the addition of 5 μl of a solution of TR-FRET detection reagents (0.2 μM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.1 nM (20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and IC50 values were calculated by a 4 parameter fit using an inhouse software.

2b. CDK2/CycE High ATP Kinase Assay

CDK2/CycE-inhibitory activity of compounds of the present invention at 2 mM adenosine-tri-phosphate (ATP) was quantified employing the CDK2/CycE TR-FRET (TR-FRET=Time Resolved Fluorescence Energy Transfer) assay as described in the following paragraphs.

Recombinant fusion proteins of GST and human CDK2 and of GST and human CycE, expressed in insect cells (Sf9) and purified by Glutathion-Sepharose affinity chromatography, were purchase from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI peptide technologies (Berlin, Germany).

For the assay 50 n1 of a 100 fold concentrated solution of the test compound in DMSO was pipetted into a black low volume 384 well microtiter plate (Greiner Bio-One, Frickenhausen, Germany), 2 μl of a solution of CDK2/CycE in aqueous assay buffer [50 mM Tris/HCl pH 8.0, 10 mM MgCl2, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 μl of a solution ATP (3.33 mM=>final conc. in the 5 μl assay volume is 2 mM) and substrate (1.25 μM final conc. in the 5 μl assay volume is 0.75 μM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 15 ng/ml. The reaction was stopped by the addition of 5 μl of a solution of TR-FRET detection reagents (0.2 μM streptavidine-XL665 [Cisbio Bioassays, Codolet, France] and 1 nM anti-RB(pSer807/pSer811)-antibody from BD Pharmingen [#558389] and 1.2 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm wer measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and IC50 values were calculated by a 4 parameter fit using an inhouse software.

3. Proliferation Assay:

Cultivated tumour cells (HeLa, human cervical tumour cells, ATCC CCL-2; NCI-H460, human non-small cell lung carcinoma cells, ATCC HTB-177; A2780, human ovarian carcinoma cells, ECACC #93112519; DU 145, hormone-independent human prostate carcinoma cells, ATCC HTB-81; HeLa-MaTu-ADR, multidrug-resistant human cervical carcinoma cells, EPO-GmbH Berlin; Caco-2, human colorectal carcinoma cells, ATCC HTB-37; B16F10, mouse melanoma cells, ATCC CRL-6475) were plated at a density of 5,000 cells/well (DU145, HeLa-MaTu-ADR), 3,000 cells/well (NCI-H460, HeLa), 2,500 cells/well (A2780), 1,500 cells/well (Caco-2), or 1,000 cells/well (B16F10) in a 96-well multititer plate in 200 µL of their respective growth medium supplemented 10% fetal calf serum. After 24 hours, the cells of one plate (zero-point plate) were stained with crystal violet (see below), while the medium of the other plates was replaced by fresh culture medium (200 µl), to which the test substances were added in various concentrations (0 µM, as well as in the range of 0.001-10 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were stained by adding 100 µl/measuring point of a 0.1% crystal violet solution (pH 3.0). After three washing cycles of the stained cells with water, the plates were dried at room temperature. The dye was dissolved by adding 100 µl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 µm) cells (=100%). The $IC_{50}$ values (inhibitory concentration at 50% of maximal effect) were determined by means of a 4 parameter fit.

Non-adherent MOLM-13 human acute myeloid leukemia cells (DSMZ ACC 554) were seeded at a density of 5,000 cells/well in a 96-well multititer plate in 100 µL of growth medium supplemented 10% fetal calf serum. After 24 hours, cell viability of one plate (zero-point plate) was determined with the Cell Titre-Glo Luminescent Cell Viability Assay (Promega), while 50 µL of test compound containing medium was added to the wells of the other plates (final concentrations in the range of 0.001-10 µM and DMSO controls; the final concentration of the solvent dimethyl sulfoxide was 0.5%). Cell viability was assessed after 72-hour exposure with the Cell Titre-Glo Luminescent Cell Viability Assay (Promega). $IC_{50}$ values (inhibitory concentration at 50% of maximal effect) were determined by means of a 4 parameter fit on measurement data which were normalized to vehicle (DMSO) treated cells (=100%) and measurement readings taken immediately before compound exposure (=0%).

4. Caco-2 Permeation Assay:

Caco-2 cells (purchased from DSMZ Braunschweig, Germany) were seeded at a density of $4.5 \times 10^4$ cells per well on 24 well insert plates, 0.4 µm pore size, and grown for 15 days in DMEM medium supplemented with 10% fetal bovine serum, 1% GlutaMAX (100×, GIBCO), 100 U/mL penicillin, 100 µg/mL streptomycin (GIBCO) and 1% non essential amino acids (100×). Cells were maintained at 37° C. in a humified 5% CO2 atmosphere. Medium was changed every 2-3 day. Before running the permeation assay, the culture medium was replaced by a FCS-free hepes-carbonate transport buffer (pH 7.2). For assessment of monolayer integrity the transepithelial electrical resistance (TEER) was measured. Test compounds were predissolved in DMSO and added either to the apical or basolateral compartment in final concentration of 2 µM in transport buffer. Before and after 2 h incubation at 37° C. samples were taken from both compartments. Analysis of compound content was done after precipitation with methanol by LC/MS/MS analysis. Permeability (Papp) was calculated in the apical to basolateral (A→B) and basolateral to apical (B→A) directions. The apparent permeability was calculated using following equation:

$$Papp = (Vr/Po)(1/S)(P2/t)$$

Where Vr is the volume of medium in the receiver chamber, Po is the measured peak area or height of the test drug in the donor chamber at t=o, S the surface area of the monolayer, P2 is the measured peak area of the test drug in the acceptor chamber after 2 h of incubation, and t is the incubation time. The efflux ratio basolateral (B) to apical (A) was calculated by dividing the Papp B-A by the Papp A-B. In addition the compound recovery was calculated. The following reference compounds were used for the classification of the permeability class: Antipyrine, Pyrazosin, Verapamil, Fluvastatin, Cimetidine, Ranitidine, Atenolol, Sulfasalazine.

5. Carbonic Anhydrase Assay

The principle of the assay is based on the hydrolysis of 4-nitrophenyl acetate by carbonic anhydrases (Pocker & Stone, Biochemistry, 1967, 6, 668), with subsequent photometric determination of the dye product 4-nitrophenolate at 400 nm by means of a 96-channel spectral photometer.

2 µL of the test compounds, dissolved in DMSO (100-fold final concentration), in a concentration range of 0.03-10 µmol/L (final), was pipetted as quadruplicates into the wells of a 96-hole microtiter plate. Wells that contained the solvent without test compounds were used as reference values (1. Wells without carbonic anhydrase for correction of the non-enzymatic hydrolysis of the substrate, and 2. Wells with carbonic anhydrase for determining the activity of the non-inhibited enzyme).

188 µL of assay buffer (10 mmol/L of Tris/HCl, pH 7.4, 80 mmol/L of NaCl), with or without 3 units/well of carbonic anhydrase-1 [=human carbonic anhydrase-1 (Sigma, #C4396)] in order to determine carbonic anhydrase-1 inhibition or 3 units/well of carbonic anhydrase-2 [=human carbonic anhydrase-2 (Sigma, #C6165)] for measuring carbonic anhydrase-2 inhibition, was pipetted into the wells of the microtiter plate. The enzymatic reaction was started by the addition of 10 microL of the substrate solution (1 mmol/L of 4-nitrophenyl acetate (Fluka #4602), dissolved in anhydrous acetonitrile (final substrate concentration: 50 µmol/L). The plate was incubated at room temperature for 15 minutes. Absorption was measured by photometry at a wavelength of 400 nm. The enzyme inhibition was calculated after the measured values were normalized to the absorption of the reactions in the wells without enzyme (=100% inhibition) and to the absorption of reactions in the wells with non-inhibited enzyme (=0% inhibition). $IC_{50}$ values were determined by means of a 4 parameter fit using the company's own software.

PREPARATIVE EXAMPLES

Syntheses of Compounds

The syntheses of the 5-fluoro-N-(pyridin-2-yl)pyridin-2-amine derivatives according to the present invention can be preferably carried out according to the general synthetic sequence, shown in schemes 1, 2, and 3.

Scheme 1 illustrates the synthesis of early intermediates of formula (3). 2-Chloro-5-fluoro-4-iodopyridine (CAS No.: 884494-49-9; 1) is reacted with a boronic acid derivative $R^2$—$B(OR)_2$ of formula (2), wherein $R^2$ is as defined for the compound of general formula (I), to give a compound of formula (3). The boronic acid derivative (2) may be a boronic acid (R=—H) or an ester of the boronic acid, e.g. its isopropyl ester (R=—$CH(CH_3)_2$), preferably an ester derived from pinacol in which the boronic acid intermediate forms a 2-aryl-4,4,5,5-tetramethyl-1,3,2-dioxaborolane (R—R=—$C(CH_3)_2$—$C(CH_3)_2$—). The coupling reaction is catalyzed by palladium catalysts, e.g. by Pd(0) catalysts like tetrakis(triphenylphosphine)palladium(0) [$Pd(PPh_3)_4$], tris(dibenzylideneacetone)di-palladium(0) [$Pd_2(dba)_3$], or by Pd(II) catalysts like dichlorobis(triphenylphosphine)-palladium(II) [$Pd(PPh_3)_2Cl_2$], palladium(II) acetate and triphenylphosphine or by 1,1'-bis-(diphenylphosphino)ferrocene] dichloropalladium(II).

The reaction is preferably carried out in a mixture of a solvent like 1,2-dimethoxyethane, dioxane, DMF, DME, THF, or isopropanol with water and in the presence of a base like potassium carbonate, sodium bicarbonate or potassium phosphate.

(review: D. G. Hall, Boronic Acids, 2005 WILEY-VCH Verlag GmbH & Co. KGaA, Weinheim, ISBN 3-527-30991-8 and references cited therein).

The reaction is performed at temperatures ranging from room temperature (=20° C.) to the boiling point of the respective solvent. Further on, the reaction can be performed at temperatures above the boiling point using pressure tubes and a microwave oven. The reaction is preferably completed after 1 to 36 hours of reaction time.

carboxy function with suitable reducing agents, e.g. borane-THF-complex, leads to pyridinemethanol derivatives of formula (5).

Starting materials of formula (4) are either commercially available or accessible e.g. from 2-oxo-1,2-dihydropyridine-4-carboxylic acids (see for example: a) WO2007/077005 or b) Dulla et al., Bioorganic and Medicinal Chemistry Letters, 2012, 22, 4629-35).

In the following step, said pyridinemethanol derivatives of formula (5) can be reacted with ammonia (see for example: WO2006/76131), or, alternatively, with suitable ammonia equivalents such as bis-(trimethylsilyl)-lithium amide or lithium amide (see for example: Huang et al., Organic Letters 2001, 3, 3417-9) to give 2-amino-substituted pyridinemethanol derivatives of formula (6). Depending on the reactivity of the halogen X present in the pyridinemethanol derivatives of formula (5), this can be accomplished by non-catalysed aromatic nucleophilic substitution, or by using metal catalysts, such as palladium catalysts, e.g. tris(dibenzylideneacetone)dipalladium (0), in the presence of a phosphine ligand, such as 2-(dicyclohexylphosphino)-2',4',6'-triisopropylbiphenyl (see also: Huang et al., Organic Letters 2001, 3, 3417-9)

The introduction of a suitable leaving group (LG), preferably chloro or bromo, into compounds of formula (6), can be accomplished subsequently to yield intermediates of formula (7). Preferred is the herein described use of thionyl chloride in NMP or DMF and DCM for the formation of chloromethylpyridine derivatives (LG=Cl). A possibility for the formation of bromomethylpyridine derivatives (LG=Br) is the use of tetrabromomethane and triphenylphosphane in DCM (see for example: Polla et al., Bioorganic and Medicinal Chemistry, 2004, 12, 1151).

Said intermediates of formula (7) are converted into substituted sulfonylmethyl pyridine intermediates of formula (9), in which $R^1$, $R^3$ and $R^4$ are as defined for the compound of general formula (I), by reacting with sulfinate salts of the formula (8), in which $R^1$ is as defined for the compound of general formula (I) and in which $M^+$ stands for a cation of an alkali metal, such as sodium, potassium or cesium (see for example: Castanedo et al., Bioorganic and Medicinal Chemistry Letters, 2010, 20, 6748-53).

Scheme 1

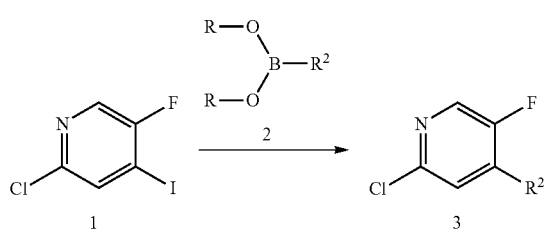

Scheme 2 shows the synthesis of substituted sulfonylmethyl pyridine intermediates of formula (9), in which $R^1$, $R^3$ and $R^4$ are as defined for the compound of general formula (I). Starting from 2-halogenated pyridine-4-carboxylic acids of formula (4), in which $R^3$ and $R^4$ are as defined for the compound of general formula (I) and X represents a halogen atom, e.g. fluoro, chloro or bromo, the reduction of the Scheme 2

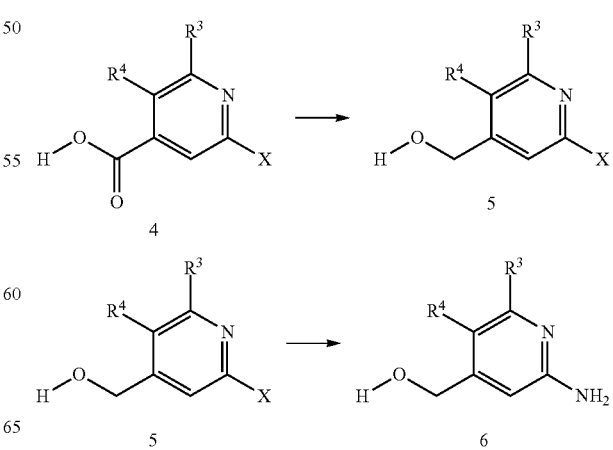

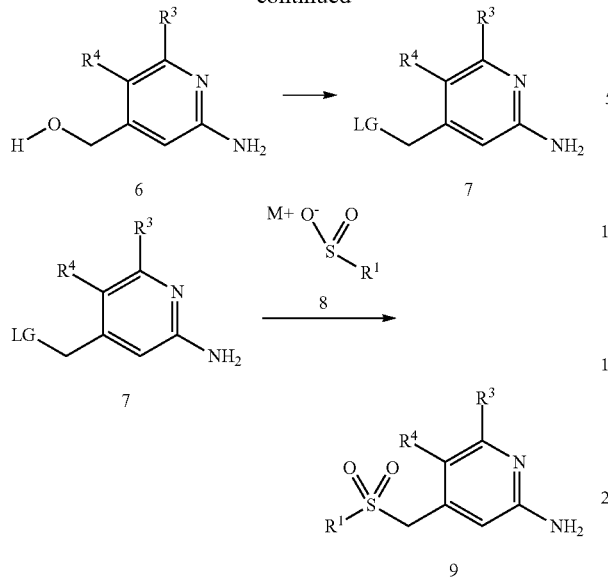

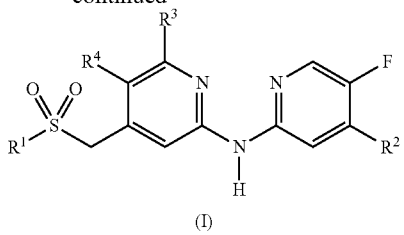

Scheme 3 depicts the assembly of compounds of general formula (I) from intermediates of formula (3), in which $R^2$ is as defined for the compound of general formula (I), and intermediates of formula (9), in which $R^1$, $R^3$ and $R^4$ are as defined for the compound of general formula (I). This can be accomplished by a Palladium-catalysed C—N cross-coupling reaction (for a review on C—N cross coupling reactions see for example: a) L. Jiang, S. L. Buchwald in 'Metal-Catalyzed Cross-Coupling Reactions', $2^{nd}$ ed.: A. de Meijere, F. Diederich, Eds.: Wiley-VCH: Weinheim, Germany, 2004).

Preferred is the herein described use of t-BuXPhos derived precatalysts, preferably chloro(2-dicyclohexylphosphino-2',4',6'-tri-iso-propyl-1,1'-biphenyl) [2-(2-aminoethyl)phenyl]palladium(II) methyl-tert-butylether adduct and 2-(dicyclohexylphosphino)-2',4',6'-triisopropylbiphenyl as catalyst/ligand system, an alkali salt of carbonic or phosphoric acid, preferably potassium phosphate, in a mixture comprising an aromatic or partially aromatic hydrocarbon, preferably toluene, and an amide selected from N,N-dimethylformamide, N,N-dimethylacetamide and N-methylpyrrolidinone, preferably N-methylpyrrolidinone, as a solvent, at a temperature between 50 and 180° C., preferably 80 and 160° C., more preferably 120 and 150° C.

Alternatively, said Palladium-catalyzed C—N cross-coupling reaction can be accomplished using tris(dibenzylideneacetone)dipalladium(0), (9,9-dimethyl-9H-xanthene-4,5-diyl)bis(diphenylphosphane) and cesium carbonate in dioxane, performing the reaction under an atmosphere of argon for 3-48 hours at 100° C. in a microwave oven or in an oil bath.

Scheme 4 illustrates an alternative approach to the 5-fluoro-N-(pyridin-2-yl)pyridin-2-amine derivatives according to the present invention.

Herein, a compound of formula (3), in which $R^2$ is as defined for the compound of general formula (I), can be reacted with a suitable pyridin-2-amine of formula (10), in which $R^1$, $R^3$ and $R^4$ are as defined for the compound of general formula (I), to give a compound of formula (11). This coupling reaction can be carried out by a Palladium-catalyzed C—N cross-coupling reactions (for a review on C—N cross coupling reactions see for example: a) L. Jiang, S. L. Buchwald in 'Metal-Catalyzed Cross-Coupling Reactions', $2^{nd}$ ed.: A. de Meijere, F. Diederich, Eds.: Wiley-VCH: Weinheim, Germany, 2004), using suitable catalyst systems such as tris(dibenzylideneacetone)dipalladium(0), (9,9-dimethyl-9H-xanthene-4,5-diyl)bis(diphenylphosphane), or t-BuXPhos derived precatalysts, as described supra, in the presence of suitable inorganic bases such as cesium carbonate or potassium phosphate (see e.g. Lee et al., Tetrahedron Letters 2009, 50, 3672-4), and performing said reactions under an atmosphere of argon for 3-48 hours at 100° C. in a microwave oven or in an oil bath.

Pyridine-2-amines of formula (10) are commercially available in certain cases, or can be prepared by methods known to the person skilled in the art, e.g. from the corresponding 4-hydroxymethylpyridine-2-amine of formula (6), in which $R^3$ and $R^4$ are as defined for the compound of general formula (I), via conversion of the hydroxy group contained therein into a suitable leaving group, such as chloro or bromo, followed by nucleophilic displacement with a thiol of the general formula (14) (see scheme 5), in which $R^1$ is as defined for the compound of formula (I). If needed, the amino group present in said 4-hydroxymethylpyridine-2-amine can be protected by a suitable protecting group. Protecting groups for amino groups present in analogues and methods for their introduction and removal are well known to the person skilled in the art, see e.g. T. W. Greene and P. G. M. Wuts in: Protective Groups in Organic Synthesis, $3^{rd}$ edition, Wiley (1999).

Subsequently, a compound of formula (5), in which $R^1$, $R^2$, $R^3$ and $R^4$ are as defined for the compound of general formula (I), can be oxidized to the corresponding sulfone of formula (I), preferably using potassium permanganate in acetone at a temperature between 40 and 70° C.

Scheme 3

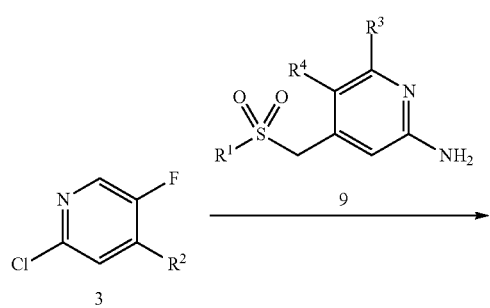

Scheme 4

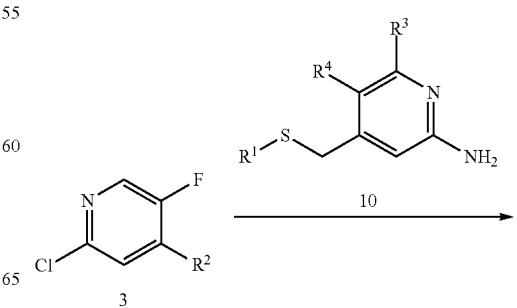

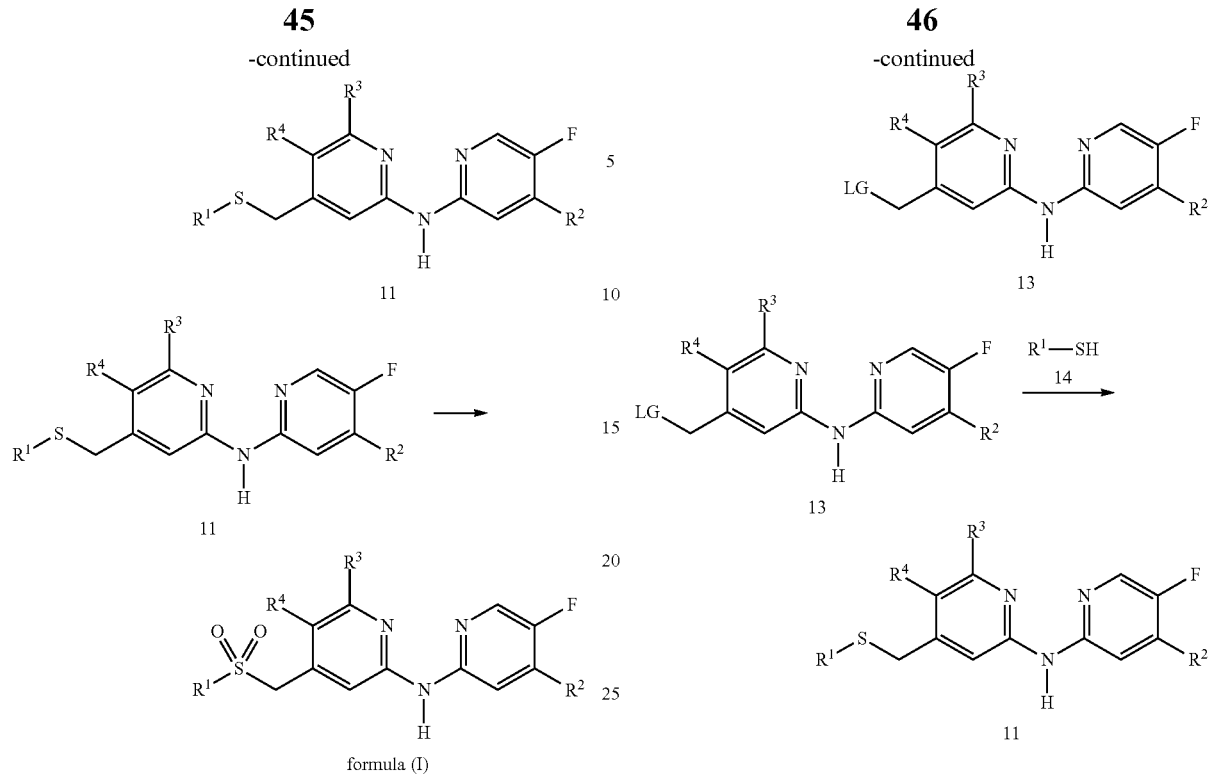

formula (I)

A further alternative synthesis approach to the 5-fluoro-N-(pyridin-2-yl)pyridin-2-amine derivatives according to the present invention is described in scheme 5.

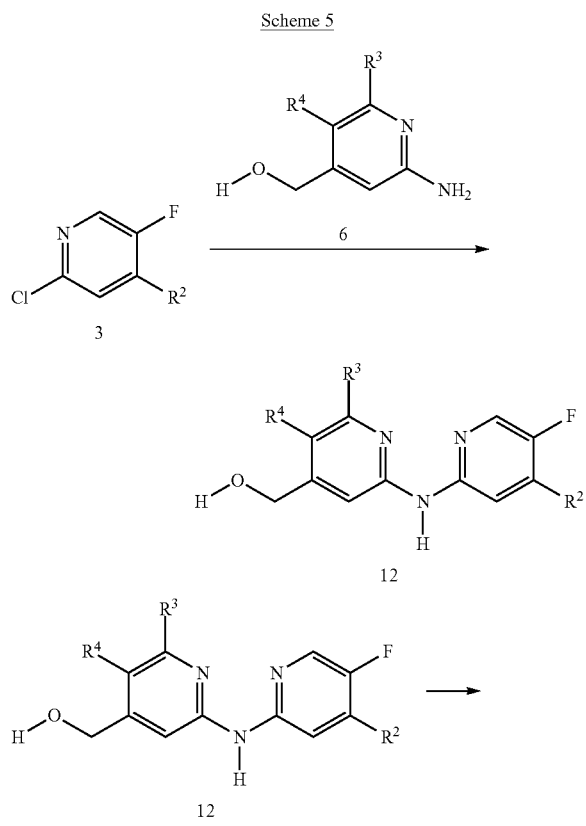

Herein, a compound of formula (3), in which $R^2$ is as defined for the compound of general formula (I), can be reacted with a suitable pyridin-2-amine of formula (6), in which $R^3$ and $R^4$ are as defined for the compound of general formula (I), to give a compound of formula (12). This coupling reaction can be carried out by a Palladium-catalyzed C—N cross-coupling reactions (for a review on C—N cross coupling reactions see for example: a) L. Jiang, S. L. Buchwald in 'Metal-Catalyzed Cross-Coupling Reactions', $2^{nd}$ ed.: A. de Meijere, F. Diederich, Eds.: Wiley-VCH: Weinheim, Germany, 2004), using suitable catalyst systems such as tris(dibenzylideneacetone)dipalladium(0), (9,9-dimethyl-9H-xanthene-4,5-diyl)bis(diphenylphosphane), or t-BuXPhos derived precatalysts in the presence of suitable inorganic bases such as cesium carbonate or potassium phosphate phosphate (see e.g. Lee et al., Tetrahedron Letters 2009, 50, 3672-4), and performing said reactions under an atmosphere of argon for 3-48 hours at 100° C. in a microwave oven or in an oil bath.

Pyridine-2-amines of formula (6) are commercially available in certain cases, or can be prepared by methods known to the person skilled in the art, e.g. by reduction of the corresponding carboxylic acids or esters thereof.

In a second step, a compound of formula (12), in which $R^2$, $R^3$ and $R^4$ are as defined for the compound of general formula (I), can be converted to a compound of formula (13), in which $R^2$, $R^3$ and $R^4$ are as defined for the compound of general formula (I) and in which LG represents a leaving group, preferably chloro or bromo. Preferred is the use of thionyl chloride in NMP or DMF and DCM for the formation of the respective chloromethyl pyridines (LG=Cl). A possibility for the formation of the respective bromomethyl pyridines (LG=Br) is the use of tetrabromomethane and triphenylphosphane in DCM (see for example: Polla et al, Bioorganic and Medicinal Chemistry, 2004, 12, 1151).

In a third step, a compound of formula (13) can be converted to a corresponding thioether of formula (11), in which $R^1$, $R^2$, $R^3$ and $R^4$ are as defined for the compound of general formula (I), by reaction with suitable thiols of formula (14), in which $R^1$ is as defined for the compound of formula (I), under basic conditions (see for example: Sammond et al, Bioorg. Med. Chem. Lett. 2005, 15, 3519). Thiols of formula (14) are known to the person skilled in the art and are commercially available in considerable variety.

In the final step, the thioether of formula (11) is oxidized to the corresponding sulfone of formula (I) as described in scheme 4.

Preparation of Compounds:

Abbreviations Used in the Description of the Chemistry and in the Examples that Follow are:

br (broad); CDCl₃ (deuterated chloroform); cHex (cyclohexane); d (doublet); DCM (dichloromethane); DIPEA (di-iso-propylethylamine); DME (1,2-dimethoxyethane), DMF (dimethylformamide); DMSO (dimethyl sulfoxide); eq (equivalent); ES (electrospray); EtOAc (ethyl acetate); EtOH (ethanol); iPrOH (iso-propanol); mCPBA (meta-chloroperoxybenzoic acid), MeCN (acetonitrile), MeOH (methanol); MS (mass spectrometry); NBS (N-bromosuccinimide), NMP (N-Methylpyrrolidin-2-one), NMR (nuclear magnetic resonance); p (pentet); Pd(dppf)Cl₂ ([1,1'-bis(diphenylphosphino)ferrocene]dichloro palladium(II) complex with dichloromethane); iPrOH (iso-propanol); q (quartet); RT (room temperature); s (singlet); sat. aq. (saturated aqueous); SiO₂ (silica gel); TFA (trifluoroacetic acid); TFAA (trifluoroacetic anhydride), THF (tetrahydrofuran); tr (triplet).

Chemical Naming:

The IUPAC names of the examples were generated using the program 'ACD/Name batch version 12.01' from ACD LABS.

Salt Stoichiometry:

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "xHCl", "xCF₃COOH", "xNa⁺", for example, are to be understood as not a stoichiometric specification, but solely as a salt form.

Preparative HPLC: Method 1

| System: | Waters Autopurificationsystem: Pump 2545, |
| | Sample Manager 2767, CFO, DAD 2996, |
| | ELSD 2424, SQD 3001 |
| Column: | XBrigde C18 5 μm 100 × 30 mm |
| Solvent: | A = H₂O + 0.1% HCOOH |
| | B = MeCN |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO or DMF |
| Injection: | 1 × 2.5 mL |
| Detection: | DAD scan range 210-400 nm |
| | MS ESI+, ESI−, scan range 160-1000 m/z |

Example 1

5-Fluoro-4-(4-fluoro-1-benzofuran-7-yl)-N-{4-[(methylsulfonyl)methyl]pyridin-2-yl}pyridin-2-amine

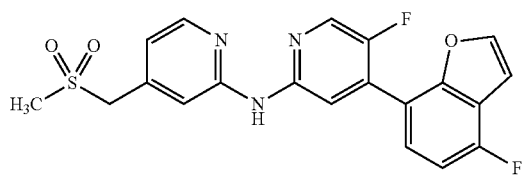 [SMILES: CS(=O)(=O)Cc1ccnc(Nc2cc(-c3ccc(F)c4ccoc34)c(F)cn2)c1]

Preparation of Intermediate 1.1

2-Chloro-5-fluoro-4-(4-fluoro-1-benzofuran-7-yl) pyridine

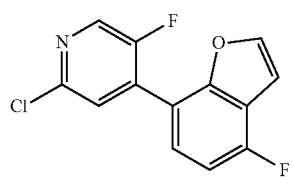 [SMILES: Fc1cnc(Cl)cc1-c1ccc(F)c2ccoc12]

Under an atmosphere of argon, a mixture of 2-chloro-5-fluoro-4-iodopyridine (4.32 g; 16.29 mmol; Manchester Organics, CAS #884494-49-9), (4-fluoro-1-benzofuran-7-yl)boronic acid (3.08 g; 16.29 mmol; ABCR, CAS #1204580-77-7) and [1,1'-bis(diphenylphosphino)ferrocene]dichloropalladium(II) dichloromethane complex (1.33 g; 1.63 mmol; Aldrich Chemical Company Inc.) in an aqueous 2M solution of potassium carbonate (24.4 mL) and 1,2-dimethoxyethane (84.6 mL) was stirred for 48 hours at ambient temperature. The batch was poured into water and diluted with ethyl acetate. After phase separation the aqueous layer was extracted with ethyl acetate. The combined organic layers were washed with diluted aqueous sodium chloride solution and dried over sodium sulfate. After evaporation the residue was purified by column chromatography on silica gel (hexane/DCM) to yield the title compound (2.93 g; 11.03 mmol).

¹H-NMR (400 MHz, DMSO-d₆): δ [ppm]=8.63 (d, 1H), 8.17 (d, 1H), 7.90 (d, 1H), 7.61 (dd, 1H), 7.31 (dd, 1H), 7.22 (d, 1H).

Preparation of Intermediate 1.2

4-(Chloromethyl)pyridin-2-amine hydrochloride

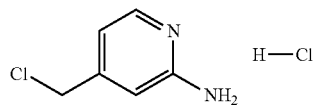

To a stirred solution of 2-aminopyridine-4-methanol (2.5 g; 19.5 mmol, CAS #105250-17-7, ABCR GmbH & CO. KG, Germany) in DCM (150 ml) at 0° C. was added dropwise thionyl chloride (14.25 mL; 19.5 mmol). The mixture was allowed to react at room temperature for 3 hours. The batch was evaporated, toluene was added and the batch was subsequently evaporated two times to yield the desired product (3.58 g; 18.19 mmol).

$^1$H-NMR (400 MHz, DMSO-$d_6$): δ [ppm]=14.03 (br. s., 1H), 8.29 (br. s., 2H), 7.95 (d, 1H), 7.06 (d, 1H), 6.84 (dd, 1H), 4.81 (s, 2H).

Preparation of Intermediate 1.3

4-[(Methylsulfonyl)methyl]pyridin-2-amine

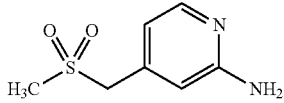

To a solution of 4-(chloromethyl)pyridin-2-amine hydrochloride (1 g; 5 mmol; Intermediate 1.2) in DMF (40 ml) sodium methanesulfinate (2.73 g; 25.4 mmol; ABCR GmbH & CO. KG, Germany) was added. The batch was stirred at 60° C. for 8 hours. The major amount of DMF was distilled of and the residue was partitioned between DCM (250 ml) and aqueous 2M solution of potassium carbonate (250 ml). After phase separation the aqueous phase was extracted with DCM. The combined organic layers were dried (sodium sulfate), filtered and concentrated to give the crude product. Purification by column chromatography on silica gel (hexane/ethyl acetate) yielded the title compound (525 mg; 2.79 mmol).

$^1$H-NMR (400 MHz, DMSO-$d_6$): δ [ppm]=7.89 (d, 1H), 6.50 (dd, 1H), 6.45 (s, 1H), 6.02 (s, 2H), 4.34 (s, 2H), 2.93 (s, 3H).

Preparation of End Product

A mixture of 4-[(methylsulfonyl)methyl]pyridin-2-amine (60 mg; 0.319 mmol; Intermediate 1.3), 2-chloro-5-fluoro-4-(4-fluoro-1-benzofuran-7-yl)pyridine (70.6 mg; 0.266 mmol; Intermediate 1.1), chloro(2-dicyclohexylphosphino-2',4',6'-tri-iso-propyl-1,1'-biphenyl) [2-(2-aminoethyl)phenyl]palladium(II) methyl-tert-butylether adduct (21.9 mg; 0.027 mmol; ABCR GmbH & Co. KG) and 2-(dicyclohexylphosphino)-2',4',6'-triisopropylbiphenyl (12.6 mg; 0.027 mmol; Aldrich Chemical Company Inc.) and potassium phosphate (282 mg; 1.33 mmol) in toluene (4.5 ml) and NMP (0.5 mL) was stirred under an atmosphere of argon at 130° C. for 3 hours. After cooling, the batch was diluted with ethyl acetate and washed with aqueous sodium chloride solution. The organic phase was filtered using a Whatman filter and concentrated. The residue was purified by preparative HPLC (Method 1) to yield the title compound (45.5 mg; 0.1 mmol).

$^1$H-NMR (400 MHz, DMSO-$d_6$): δ [ppm]=9.98 (s, 1H), 8.37 (d, 1H), 8.20 (d, 1H), 8.16 (d, 1H), 8.13 (d, 1H), 7.64 (s, 1H), 7.53 (dd, 1H), 7.29 (t, 1H), 7.21 (d, 1H), 6.91 (dd, 1H), 4.52 (s, 2H), 3.01 (s, 3H).

Example 2

5-Fluoro-4-(4-fluoro-1-benzofuran-7-yl)-N-{6-fluoro-4-[(methylsulfonyl)methyl]pyridin-2-yl}pyridin-2-amine

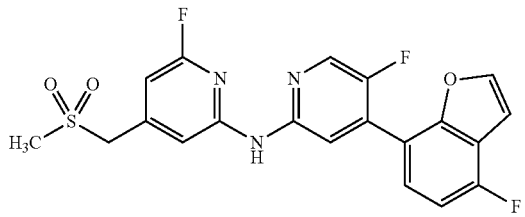 [SMILES: CS(=O)(=O)Cc1cc(F)nc(Nc2cc(-c3ccc(F)c4ccoc34)c(F)cn2)c1]

Preparation of Intermediate 2.1

(2,6-Difluoropyridin-4-yl)methanol

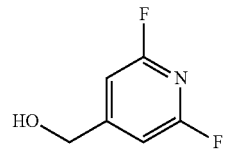

To a stirred solution of 2,6-difluoropyridine-4-carboxylic acid (5.32 g; 32.8 mmol; Matrix Scientific, CAS #88912-23-6) in THF (85 mL) at 0° C. was added a 1M solution of borane-tetrahydrofuran complex in THF (13.2 mL; 131.2 mmol). The mixture was allowed to react at RT overnight. Then, MeOH (15.9 mL) was cautiously added to the stirred mixture while cooling with an ice bath. The batch was diluted with ethyl acetate and washed with aqueous sodium hydroxide solution (1N) and saturated aqueous sodium chloride solution. The organic phase was filtered using a Whatman filter and concentrated to yield the title compound (4.85 g).

$^1$H-NMR (400 MHz, DMSO-$d_6$): δ [ppm]=7.06 (s, 2H), 5.68 (t, 1H), 4.62 (d, 2H).

Preparation of Intermediate 2.2

(2-Amino-6-fluoropyridin-4-yl)methanol

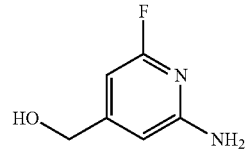

A mixture of (2,6-difluoropyridin-4-yl)methanol (330 mg; 2.27 mmol, intermediate 2.1) and 33% w/w aqueous solution of ammonia (19.8 ml) was placed into a microwave tube. The mixture was allowed to react at 110° C. for 6 hours in the sealed tube under microwave irradiation. Then, the mixture was diluted with water and extracted with ethyl acetate. The combined organic layers were washed with saturated aqueous sodium chloride solution and dried over sodium sulfate. After evaporation the residue was purified by column chromatography on silica gel (dichloromethane/methanol) to yield the title compound (209 mg, 1.41 mmol).

$^1$H-NMR (400 MHz, DMSO-$d_6$): δ [ppm]=6.28 (dd, 1H), 6.22 (s, 2H), 5.99 (s, 1H), 5.28 (t, 1H), 4.37 (d, 2H).

Preparation of Intermediate 2.3

4-(Chloromethyl)-6-fluoropyridin-2-amine

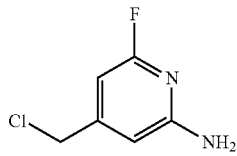

To a stirred solution of (2-amino-6-fluoropyridin-4-yl)methanol (194 mg; 1.36 mmol, intermediate 2.2) in DCM (6.6 ml) and NMP (0.44 ml) at 0° C. was added dropwise thionyl chloride (0.25 mL; 3.41 mmol). The mixture was allowed to react at room temperature overnight. The batch was diluted with aqueous sodium bicarbonate solution and aqueous sodium chloride solution and extracted three times with DCM. The combined organic phases were filtered, dried over sodium sulfate, and concentrated. The crude material was purified by column chromatography on silica gel (dichloromethane/methanol) to yield the desired product (161 mg; 0.94 mmol).

$^1$H-NMR (400 MHz, DMSO-$d_6$): δ [ppm]=6.45 (s, 1H), 6.34 (d, 1H), 6.13 (s, 1H), 4.61 (s, 2H).

Preparation of Intermediate 2.4

6-Fluoro-4-[(methylsulfonyl)methyl]pyridin-2-amine

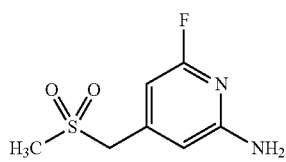

To a solution of 4-(chloromethyl)-6-fluoropyridin-2-amine (50 mg; 0.311 mmol; Intermediate 2.3) in DMF (2.5 ml) sodium methanesulfinate (167 mg; 1.55 mmol; ABCR GmbH & CO. KG, Germany) was added. The batch was stirred at 60° C. for 8 hours. The major amount of DMF was distilled of and the residue was partitioned between DCM (250 ml) and aqueous 2M solution of potassium carbonate (250 ml). After phase separation the aqueous phase was extracted with DCM. The combined organic layers were dried (sodium sulfate), filtered and concentrated to give the crude product. Purification by column chromatography on silica gel (hexane/ethyl acetate) yielded the title compound (48.8 mg; 0.23 mmol).

$^1$H-NMR (400 MHz, DMSO-$d_6$): δ [ppm]=6.47 (s, 1H), 6.33 (d, 1H), 6.13 (s, 1H), 4.40 (s, 2H), 2.95 (s, 3H).

Preparation of End Product:

A mixture of 6-fluoro-4-[(methylsulfonyl)methyl]pyridin-2-amine (48.8 mg; 0.23 mmol; Intermediate 2.4), 2-chloro-5-fluoro-4-(4-fluoro-1-benzofuran-7-yl)pyridine (50.5 mg; 0.19 mmol; Intermediate 1.1), chloro(2-dicyclohexylphosphino-2',4',6'-tri-iso-propyl-1,1'-biphenyl) [2-(2-aminoethyl)phenyl]palladium(II) methyl-tert-butylether adduct (15.7 mg; 0.019 mmol; ABCR GmbH & Co. KG) and 2-(dicyclohexylphosphino)-2',4',6'-triisopropylbiphenyl (9.1 mg; 0.019 mmol; Aldrich Chemical Company Inc.) and potassium phosphate (202 mg; 1.33 mmol) in toluene (4.3 ml) and NMP (0.33 mL) was stirred under an atmosphere of argon at 130° C. for 3 hours. After cooling, the batch was diluted with ethyl acetate and washed with aqueous sodium chloride solution. The organic phase was filtered using a Whatman filter and concentrated. The residue was purified by preparative HPLC (Method 1) to yield the title compound (16.8 mg; 0.04 mmol).

$^1$H-NMR (400 MHz, DMSO-$d_6$): δ [ppm]=10.27 (s, 1H), 8.41 (d, 1H), 8.15 (d, 1H), 7.93 (d, 1H), 7.66 (s, 1H), 7.54 (dd, 1H), 7.30 (t, 1H), 7.21 (d, 1H), 6.61 (s, 1H), 4.60 (s, 2H), 3.03 (s, 3H).

Example 3

5-Fluoro-4-(4-fluoro-1-benzofuran-7-yl)-N-{6-methyl-4-[(methylsulfonyl)methyl]pyridin-2-yl}pyridin-2-amine

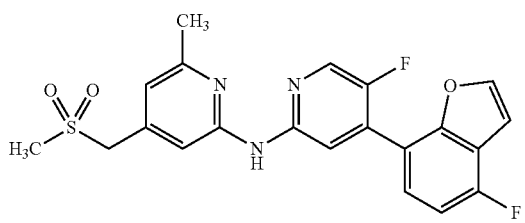 [SMILES: Cc1cc(CS(C)(=O)=O)cc(Nc2cc(-c3ccc(F)c4ccoc34)c(F)cn2)n1]

Preparation of Intermediate 3.1

(2-Chloro-6-methylpyridin-4-yl)methanol

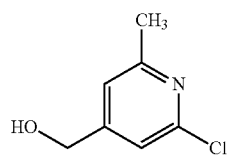

To a stirred solution of 2-chloro-6-methylisonicotinic acid (2 g; 11.1 mmol; ACROS Organics, CAS #25462-85-5) in THF (29 mL) at 0° C. was added a 1M solution of borane-tetrahydrofuran complex in THF (33.2 mL; 33.2 mmol). The mixture was allowed to react at RT overnight. Then, the batch was diluted with EtOAc (350 mL) and aqueous sodium hydroxide solution (1N; 330 ml) was added. After phase separation the organic layer was washed with saturated aqueous sodium chloride solution, dried (sodium sulfate), and concentrated to yield the title compound (1.67 g).

$^1$H-NMR (400 MHz, DMSO-$d_6$): δ [ppm]=7.19 (d, 1H), 5.48 (t, 1H), 4.51 (d, 2H), 2.43 (s, 3H).

Preparation of Intermediate 3.2

(2-Amino-6-methylpyridin-4-yl)methanol

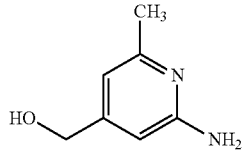

A solution of lithium bis(trimethylsilyl)amide in THF (1M; 12.69 mL; 12.69 mmol; Aldrich Chemical Company Inc.) was added to a mixture of (2-chloro-6-methylpyridin-4-yl)methanol (1 g; 6.34 mmol, intermediate 3.1), tris(dibenzylideneacetone)dipalladium (0) (116.6 mg; 0.127 mmol; Aldrich Chemical Company Inc.) and 2-(dicyclohexylphosphino)-2',4',6'-triisopropylbiphenyl (120.9 mg; 0.254 mmol; Aldrich Chemical Company Inc.) in THF (12.5 mL) under an atmosphere of argon at room temperature. The mixture was stirred at 60° C. for 3 hours. The mixture was cooled to −20° C. and 1 M hydrochloric acid was added until a pH value between 4 and 6 was reached. The mixture was slowly warmed to room temperature under stirring and aqueous sodium hydroxide solution (5N) was added to adjust a $p_H$ value between 10 and 11. After addition of brine (150 ml) the mixture was extracted with ethyl acetate. The combined organic phases were dried (sodium sulfate), filtered, and concentrated. The residue was purified by column chromatography on silica gel (ethyl acetate/methanol) to yield the title compound (600 mg; 4.34 mmol).

$^1$H-NMR (400 MHz, DMSO-$d_6$): δ [ppm]=11.08-11.05 (m, 1H), 6.26 (s, 1H), 6.22 (s, 1H), 5.69 (s, 2H), 5.12 (t, 1H), 4.31 (d, 2H), 2.19 (s, 3H).

Preparation of Intermediate 3.3

4-(Chloromethyl)-6-methylpyridin-2-amine

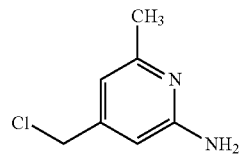

To a stirred solution of (2-amino-6-methylpyridin-4-yl)methanol (306 mg; 2.22 mmol, intermediate 3.2) in DCM (10.8 ml) and NMP (0.72 ml) at 0° C. was added dropwise thionyl chloride (0.4 mL; 5.54 mmol). The mixture was allowed to react at room temperature overnight. The batch was diluted with aqueous sodium bicarbonate solution and aqueous sodium chloride solution and extracted three times with DCM. The combined organic layers were filtered, dried over sodium sulfate, and concentrated. The crude material was purified by column chromatography on silica gel (ethyl acetate/methanol) to yield the desired product (360 mg; 1.77 mmol).

$^1$H-NMR (400 MHz, DMSO-$d_6$): δ [ppm]=6.36 (s, 1H), 6.27 (s, 1H), 5.94 (br. s., 2H), 4.53 (s, 2H), 2.24-2.20 (m, 3H).

Preparation of Intermediate 3.4

6-Methyl-4-[(methylsulfonyl)methyl]pyridin-2-amine

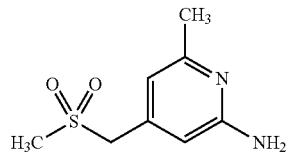

To a solution of 4-(chloromethyl)-6-methylpyridin-2-amine (100 mg; 0.619 mmol; Intermediate 3.3) in DMF (2.5 ml) sodium methanesulfinate (332 mg; 3.09 mmol; ABCR GmbH & CO. KG, Germany) was added. The batch was stirred at 60° C. for 3 hours. DMF was distilled of and the resulting residue was purified by column chromatography on silica gel (hexanes/ethyl acetate/methanol) to yield the title compound (82.8 mg; 0.41 mmol).

$^1$H-NMR (400 MHz, DMSO-$d_6$): δ [ppm]=6.36 (s, 1H), 6.26 (s, 1H), 5.93 (s, 2H), 4.28 (s, 2H), 2.92 (s, 3H), 2.22 (s, 3H).

Preparation of End Product:

A mixture of 6-methyl-4-[(methylsulfonyl)methyl]pyridin-2-amine (40 mg; 0.198 mmol; Intermediate 3.4), 2-chloro-5-fluoro-4-(4-fluoro-1-benzofuran-7-yl)pyridine (43.7 mg; 0.165 mmol; Intermediate 1.1), chloro(2-dicyclohexylphosphino-2',4',6'-tri-iso-propyl-1,1'-biphenyl)[2-(2-aminoethyl)phenyl]palladium(II) methyl-tert-butylether adduct (13.6 mg; 0.016 mmol; ABCR GmbH & Co. KG) and 2-(dicyclohexylphosphino)-2',4',6'-triisopropylbiphenyl (7.8 mg; 0.016 mmol; Aldrich Chemical Company Inc.) and potassium phosphate (175 mg; 0.824 mmol) in toluene (3.8 ml) and NMP (0.28 mL) was stirred under an atmosphere of argon at 130° C. for 3 hours. After cooling, the batch was diluted with ethyl acetate and washed with aqueous sodium chloride solution. The organic phase was filtered using a Whatman filter and concentrated. The residue was purified by preparative HPLC (Method 1) to yield the title compound (39.7 mg; 0.09 mmol).

$^1$H-NMR (400 MHz, DMSO-$d_6$): δ [ppm]=9.92 (s, 1H), 8.35 (d, 1H), 8.20 (d, 1H), 8.17 (d, 1H), 7.58-7.49 (m, 2H), 7.29 (dd, 1H), 7.21 (d, 1H), 6.78 (s, 1H), 4.46 (s, 2H), 3.01 (s, 3H), 2.37 (s, 3H).

Example 4

5-Fluoro-4-(4-fluoro-1-benzofuran-7-yl)-N-{4-[(methylsulfonyl)methyl]-6-(trifluoromethyl)pyridin-2-yl}pyridin-2-amine

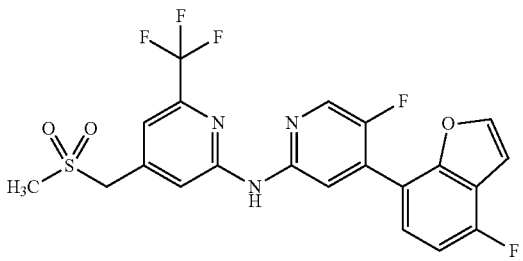 [SMILES: CS(=O)(=O)Cc1cc(Nc2cc(-c3ccc(F)c4ccoc34)c(F)cn2)nc(C(F)(F)F)c1]

Preparation of Intermediate 4.1

[2-Amino-6-(trifluoromethyl)pyridin-4-yl]methanol

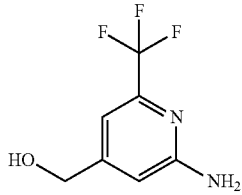 [SMILES: Nc1cc(CO)cc(C(F)(F)F)n1]

A solution of lithium bis(trimethylsilyl)amide in THF (1M; 44.9 mL; 44.9 mmol; Aldrich Chemical Company Inc.) was added to a mixture of [2-chloro-6-(trifluoromethyl)pyridin-4-yl]methanol (5 g; 22.45 mmol; Anichem Inc., North Brunswick, N.J.; CAS #1196157-41-1.), tris(dibenzylideneacetone)-dipalladium (0) (411 mg; 0.449 mmol; Aldrich Chemical Company Inc.,) and 2-(dicyclohexylphosphino)-2',4',6'-triisopropylbiphenyl (428 mg; 0.898 mmol; Aldrich Chemical Company Inc.) in THF (44.2 mL) under an atmosphere of argon at room temperature. The mixture was stirred at 60° C. for 1 hour. The mixture was cooled to −20° C. and 1 M hydrochloric acid was added until a $p_H$ between 4 and 6 was reached. The mixture was slowly warmed to room temperature under stirring and aqueous sodium hydroxide solution (5N) was added to adjust a pH between 10 and 11. After addition of brine (150 ml) the mixture was extracted with ethyl acetate. The combined organic phases were dried (sodium sulfate), filtered, and concentrated. The residue was purified by column chromatography on silica gel (ethyl acetate/methanol) to yield the title compound (3.62 g; 18.85 mmol).

$^1$H-NMR (400 MHz, DMSO-d$_6$): δ [ppm]=6.81 (s, 1H), 6.65 (s, 1H), 6.46 (s, 2H), 5.38 (t, 1H), 4.44 (d, 2H).

Preparation of Intermediate 4.2

4-(Chloromethyl)-6-(trifluoromethyl)pyridin-2-amine hydrochloride

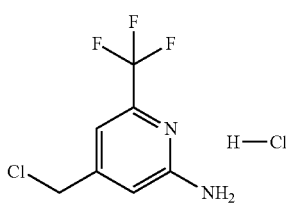

To a stirred solution of [2-amino-6-(trifluoromethyl)pyridin-4-yl]methanol (3.62 g; 18.84 mmol, intermediate 4.1) in DCM (100 ml) at 0° C. was added dropwise thionyl chloride (13.74 mL; 188.4 mmol). The mixture was allowed to react at room temperature for 3 hours. The solvent was then evaporated and the resulting slurry was filtered. The obtained solid was washed and dried to give the desired product (2.14 g).

$^1$H-NMR (400 MHz, DMSO-d$_6$): δ [ppm]=6.93 (d, 1H), 6.73 (s, 1H), 6.28-5.54 (br), 4.70 (s, 2H).

Preparation of Intermediate 4.3

4-[(Methylsulfonyl)methyl]-6-(trifluoromethyl)pyridin-2-amine

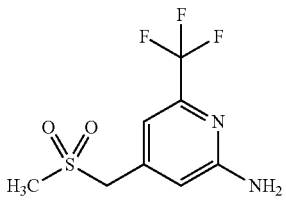 [SMILES: CS(=O)(=O)Cc1cc(N)nc(C(F)(F)F)c1]

To a solution of 4-(chloromethyl)-6-(trifluoromethyl)pyridin-2-amine hydrochloride (650 mg; Intermediate 4.3) in DMF (19.8 ml) sodium methanesulfinate (1.4 g; 13.7 mmol; ABCR GmbH & CO. KG, Germany) was added. The batch was stirred at 60° C. for 2 hours. DMF was distilled off and the resulting residue was purified by column chromatography on silica gel (hexanes/ethyl acetate) to yield the title compound (592 mg; 2.32 mmol).

$^1$H-NMR (400 MHz, DMSO-d$_6$): δ [ppm]=6.93 (d, 1H), 6.70 (s, 3H), 4.50 (s, 2H), 2.98 (s, 3H).

Preparation of End Product:

A mixture of 4-[(methylsulfonyl)methyl]-6-(trifluoromethyl)pyridin-2-amine (46.7 mg; 0.184 mmol; Intermediate 4.3), 2-chloro-5-fluoro-4-(4-fluoro-1-benzofuran-7-yl)pyridine (40 mg; 0.151 mmol; Intermediate 1.1), chloro(2-dicyclohexylphosphino-2',4',6'-tri-iso-propyl-1,1'-biphenyl)[2-(2-aminoethyl)phenyl]palladium(II) methyl-tert-butylether adduct (12.4 mg; 0.015 mmol; ABCR GmbH & Co. KG) and 2-(dicyclohexylphosphino)-2',4',6'-triisopropylbiphenyl (7.2 mg; 0.015 mmol; Aldrich Chemical Company Inc.) and potassium phosphate (160 mg; 0.753 mmol) in toluene (3.4 ml) and NMP (0.26 mL) was stirred under an atmosphere of argon at 130° C. for 3 hours. After cooling, the batch was diluted with ethyl acetate and washed with aqueous sodium chloride solution. The organic phase was filtered using a Whatman filter and concentrated. The residue was purified by preparative HPLC (Method 1) to yield the title compound (38.8 mg; 0.08 mmol).

$^1$H-NMR (400 MHz, DMSO-d$_6$): δ [ppm]=10.49 (s, 1H), 8.43 (d, 1H), 8.24 (d, 1H), 8.13 (d, 1H), 7.91 (s, 1H), 7.54 (dd, 1H), 7.37 (s, 1H), 7.31 (dd, 1H), 7.21 (d, 1H), 4.69 (s, 2H), 3.05 (s, 3H).

Example 5

4-(1-Benzofuran-7-yl)-5-fluoro-N-{4-[(methylsulfonyl)methyl]pyridin-2-yl}pyridin-2-amine

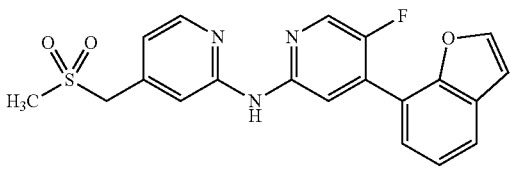 [SMILES: CS(=O)(=O)Cc1ccnc(Nc2cc(-c3cccc4ccoc34)c(F)cn2)c1]

Preparation of Intermediate 5.1

4-(1-Benzofuran-7-yl)-2-chloro-5-fluoropyridine

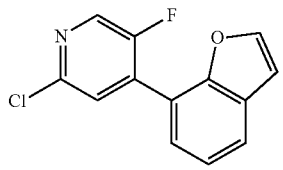 [SMILES: Fc1cnc(Cl)cc1-c1cccc2ccoc12]

Under an atmosphere of argon, a mixture of 2-chloro-5-fluoro-4-iodopyridine (1.29 g; 4.77 mmol; Manchester Organics, CAS #884494-49-9), 7-(4,4,5,5-tetramethyl-1,3,2-dioxaborolan-2-yl)-1-benzofuran (1 g; 3.97 mmol; Maybridge, CAS #1192755-14-8) and [1,1'-bis-(diphenylphosphino)ferrocene]dichloropalladium(II) dichloromethane complex (325 mg; 0.397 mmol; Aldrich Chemical Company Inc.) in an aqueous 2M solution of potassium carbonate (11.9 mL) and 1,2-dimethoxyethane (20.6 mL) was stirred for 17 hours at ambient temperature. The batch was poured into water and diluted with ethyl acetate. After phase separation the aqueous layer was extracted with ethyl acetate. The combined organic layers were washed with diluted aqueous sodium chloride solution and dried over sodium sulfate. After evaporation the residue was purified by column chromatography on silica gel (hexane/dichloromethane) to yield the title compound (930 mg; 3.76 mmol).

$^1$H-NMR (400 MHz, DMSO-$d_6$): δ [ppm]=8.63 (d, 1H), 8.10 (d, 1H), 7.90 (d, 1H), 7.85 (dd, 1H), 7.56-7.52 (m, 1H), 7.46-7.39 (m, 1H), 7.10 (d, 1H).

Preparation of End Product:

A mixture of 4-[(methylsulfonyl)methyl]pyridin-2-amine (75 mg; 0.399 mmol; Intermediate 1.3), 4-(1-benzofuran-7-yl)-2-chloro-5-fluoropyridine (82.3 mg; 0.332 mmol; Intermediate 5.1), chloro(2-dicyclohexylphosphino-2',4',6'-tri-iso-propyl-1,1'-biphenyl) [2-(2-aminoethyl)phenyl] palladium(II) methyl-tert-butylether adduct (27.4 mg; 0.033 mmol; ABCR GmbH & Co. KG) and 2-(dicyclohexylphosphino)-2',4',6'-triisopropylbiphenyl (15.9 mg; 0.033 mmol; Aldrich Chemical Company Inc.) and potassium phosphate (353 mg; 1.66 mmol) in toluene (5.6 ml) and NMP (0.62 mL) was stirred under an atmosphere of argon at 130° C. for 3 hours. After cooling, the batch was diluted with ethyl acetate and washed with aqueous sodium chloride solution. The organic phase was filtered using a Whatman filter and concentrated. The residue was purified by preparative HPLC (Method 1) to yield the title compound (42.8 mg; 0.11 mmol).

$^1$H-NMR (400 MHz, DMSO-$d_6$): δ [ppm]=9.97 (s, 1H), 8.36 (d, 1H), 8.20 (d, 1H), 8.13 (d, 1H), 8.08 (d, 1H), 7.82 (dd, 1H), 7.65 (s, 1H), 7.50-7.38 (m, 2H), 7.09 (d, 1H), 6.91 (dd, 1H), 4.52 (s, 2H), 3.01 (s, 3H).

The following Table 1 provides an overview on the compounds described in the example section:

TABLE 1

| Example No. | Structure | Name of compound |
|---|---|---|
| 1 | 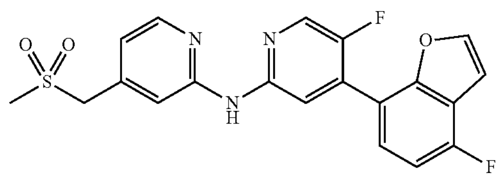 [SMILES: CS(=O)(=O)Cc1ccnc(Nc2cc(-c3ccc(F)c4ccoc34)c(F)cn2)c1] | 5-Fluoro-4-(4-fluoro-1-benzofuran-7-yl)-N-{4-[(methylsulfonyl)methyl]pyridin-2-yl}pyridin-2-amine |
| 2 | 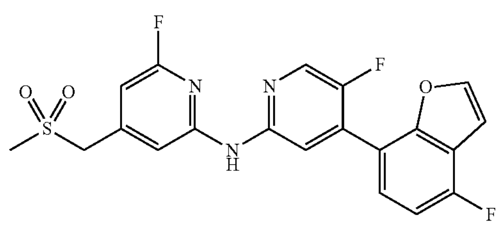 [SMILES: CS(=O)(=O)Cc1cc(F)nc(Nc2cc(-c3ccc(F)c4ccoc34)c(F)cn2)c1] | 5-Fluoro-4-(4-fluoro-1-benzofuran-7-yl)-N-{6-fluoro-4-[(methylsulfonyl)methyl]pyridin-2-yl}pyridin-2-amine |
| 3 | 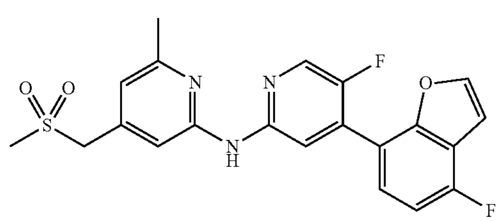 [SMILES: Cc1cc(CS(C)(=O)=O)cc(Nc2cc(-c3ccc(F)c4ccoc34)c(F)cn2)n1] | 5-Fluoro-4-(4-fluoro-1-benzofuran-7-yl)-N-{6-methyl-4-[(methylsulfonyl)methyl]pyridin-2-yl}pyridin-2-amine |
| 4 | 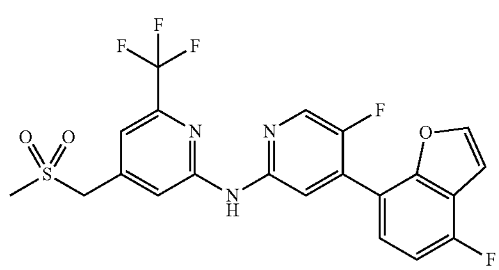 [SMILES: CS(=O)(=O)Cc1cc(Nc2cc(-c3ccc(F)c4ccoc34)c(F)cn2)nc(C(F)(F)F)c1] | 5-Fluoro-4-(4-fluoro-1-benzofuran-7-yl)-N-{4-[(methylsulfonyl)methyl]-6-(trifluoromethyl)pyridin-2-yl}pyridin-2-amine |

TABLE 1-continued

| Example No. | Structure | Name of compound |
|---|---|---|
| 5 | 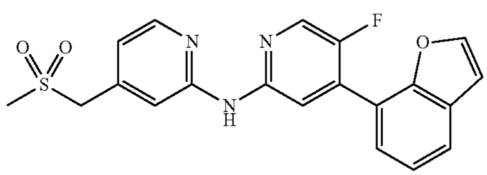 [SMILES: CS(=O)(=O)Cc1ccnc(Nc2cc(-c3cccc4ccoc34)c(F)cn2)c1] | 4-(1-Benzofuran-7-yl)-5-fluoro-N-{4-[(methylsulfonyl)methyl]pyridin-2-yl}pyridin-2-amine |

Results:

Table 2: Inhibition for CDK9 and CDK2 of compounds according to the present invention The $IC_{50}$ (inhibitory concentration at 50% of maximal effect) values are indicated in nM, "n.t." means that the compounds have not been tested in this assay.

①: Example Number
②: CDK9: CDK9/CycT1 kinase assay as described under Method 1a. of Materials and Methods
③: CDK2: CDK2/CycE kinase assay as described under Method 2a. of Materials and Methods
④: Selectivity CDK9/CDK2 according to Methods 1a. and 2a. of Materials and Methods
⑤: high ATP CDK9: CDK9/CycT1 kinase assay as described under Method 1b. of Materials and Methods
⑥: high ATP CDK2: CDK2/CycE kinase assay as described under Method 2b. of Materials and Methods
⑦: Selectivity high ATP CDK9/high ATP CDK2 according to Methods 1b. and 2b. of Materials and Methods

TABLE 2

| ① | Structure | ② | ③ | ④ | ⑤ | ⑥ | ⑦ |
|---|---|---|---|---|---|---|---|
| 1 | 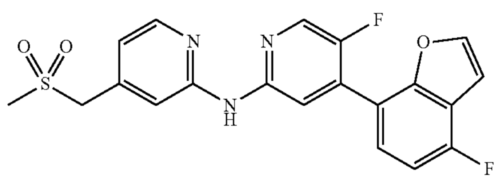 [SMILES: CS(=O)(=O)Cc1ccnc(Nc2cc(-c3ccc(F)c4ccoc34)c(F)cn2)c1] | 3 | 87 | 29 | 2 | 535 | 268 |
| 2 | 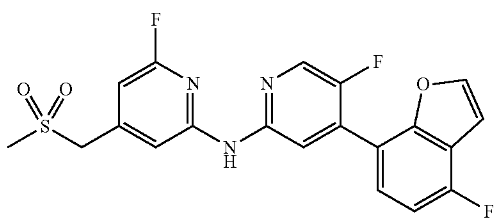 [SMILES: CS(=O)(=O)Cc1cc(F)nc(Nc2cc(-c3ccc(F)c4ccoc34)c(F)cn2)c1] | 4 | 71 | 18 | 1 | 517 | 517 |
| 3 | 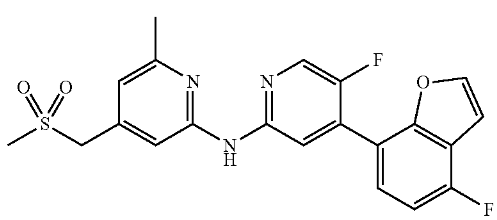 [SMILES: Cc1cc(CS(C)(=O)=O)cc(Nc2cc(-c3ccc(F)c4ccoc34)c(F)cn2)n1] | n.t. | 46 | n.t. | 0.9 | n.t. | n.t. |
| 4 | 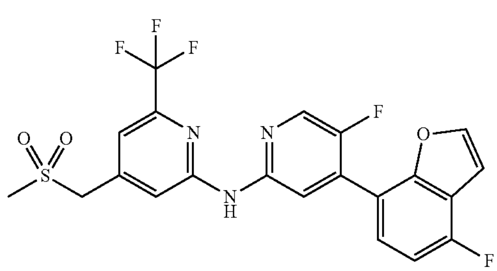 [SMILES: CS(=O)(=O)Cc1cc(Nc2cc(-c3ccc(F)c4ccoc34)c(F)cn2)nc(C(F)(F)F)c1] | n.t. | 33 | n.t. | 4 | n.t. | n.t. |

TABLE 2-continued

| ① | Structure | ② | ③ | ④ | ⑤ | ⑥ | ⑦ |
|---|---|---|---|---|---|---|---|
| 5 | 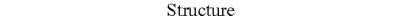 | 4 | 69 | 17 | 2 | n.t. | n.t. |

Table 3a and 3b: Inhibition of proliferation of HeLa, HeLa-MaTu-ADR, NCI-H460, DU145, Caco-2, B16F10 and A2780 cells (for corresponding indications see table 3a) by compounds according to the present invention, determined as described under Method 3. of Materials and Methods. All $IC_{50}$ (inhibitory concentration at 50% of maximal effect) values are indicated in nM, "n.t." means that the compounds have not been tested in this assay.

①: Example Number
②: Inhibition of HeLa cell proliferation
③: Inhibition of HeLa-MaTu-ADR cell proliferation
④: Inhibition of NCI-H460 cell proliferation
⑤: Inhibition of DU145 cell proliferation
⑥: Inhibition of Caco-2 cell proliferation
⑦: Inhibition of B16F10 cell proliferation
⑧: Inhibition of A2780 cell proliferation Said cell lines represent the following indications as shown in table 3a:

TABLE 3a

| Cell line | Indication |
|---|---|
| HeLa | human cervical tumour |
| HeLa-MaTu-ADR | multidrug-resistant human cervical carcinoma |
| NCI-H460 | human non-small cell lung carcinoma |
| DU145 | hormone-independent human prostate carcinoma |
| Caco-2 | human colorectal carcinoma |
| B16F10 | mouse melanoma |
| A2780 | human ovarian carcinoma |

TABLE 3b

Inhibition of cell proliferation

| ① | Structure | ② | ③ | ④ | ⑤ | ⑥ | ⑦ | ⑧ |
|---|---|---|---|---|---|---|---|---|
| 1 | 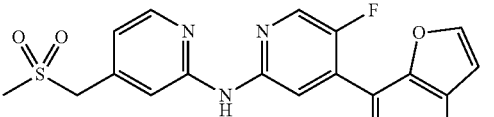 | 6 | 36 | 37 | 34 | 40 | 70 | n.t. |
| 2 | 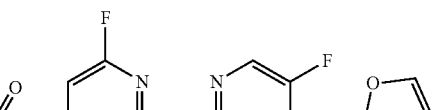 | 40 | 24 | 48 | 36 | 37 | 59 | 24 |
| 3 | 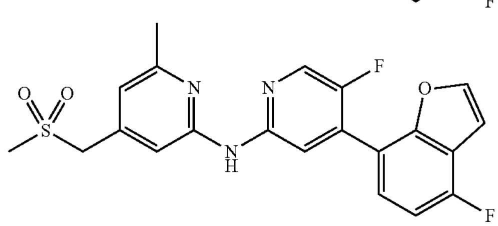 | 12 | 18 | 19 | 24 | 12 | 32 | n.t. |
| 4 | 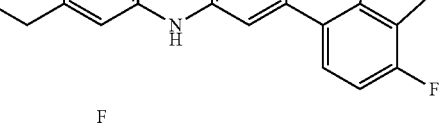 | 13 | 23 | 33 | 30 | 14 | 31 | n.t. |

TABLE 3b-continued

Inhibition of cell proliferation

| ① | Structure | ② | ③ | ④ | ⑤ | ⑥ | ⑦ | ⑧ |
|---|-----------|---|---|---|---|---|---|---|
| 5 | [structure] | 68 | 68 | 91 | 58 | 61 | 120 | n.t. |

The invention claimed is:

1. A compound of formula (I)

(I)

[structure]

wherein:
R$^1$ is a C$_1$-C$_6$-alkyl- or C$_3$-C$_5$-cycloalkyl group,
  wherein said group is optionally substituted with one substituent selected from the group consisting of hydroxy, C$_1$-C$_3$-alkyl-, fluoro-C$_1$-C$_2$-alkyl-, C$_1$-C$_3$-alkoxy-, C$_1$-C$_2$-fluoroalkoxy-, —NH$_2$, alkylamino-, dialkylamino-, cyclic amines, —OP(O)(OH)$_2$, —C(O)OH, and —C(O)NH$_2$;
R$^2$ is the group

[structure]

R$^3$ is a hydrogen atom, a fluoro atom, a chloro atom, a C$_1$-C$_3$-alkyl group or a fluoro-C$_1$-C$_3$-alkyl- group;
R$^4$ is a hydrogen atom or a fluoro atom;
R$^{5a}$ and R$^{5b}$ are independently selected from the group consisting of:
  a hydrogen atom, a fluoro atom, a chloro atom, a bromo atom, cyano, C$_1$-C$_2$-alkyl-, C$_1$-C$_2$-alkoxy-, fluoro-C$_1$-C$_2$-alkyl-, and C$_1$-C$_2$-fluoroalkoxy-; and
R$^6$ and R$^7$ are independently a group selected from selected from the group consisting of:
  a hydrogen atom, a fluoro atom, a chloro atom, a bromo atom, cyano, C$_1$-C$_2$-alkyl-, C$_1$-C$_2$-alkoxy-, fluoro-C$_1$-C$_2$-alkyl-, and C$_1$-C$_2$-fluoroalkoxy-,
or a salt thereof.

2. The compound of formula (I) according to claim 1, wherein:
R$^1$ is a C$_1$-C$_6$-alkyl- or C$_3$-C$_5$-cycloalkyl group,
  wherein said group is optionally substituted with one substituent selected from the group consisting of hydroxy, C$_1$-C$_3$-alkoxy-, —NH$_2$, alkylamino-, dialkylamino-, cyclic amines, and —OP(O)(OH)$_2$;
R$^2$ is the group

[structure]

R$^3$ is a hydrogen atom, a fluoro atom, a chloro atom, a C$_1$-C$_3$-alkyl group or a fluoro-C$_1$-C$_3$-alkyl group;
R$^4$ is a hydrogen atom or a fluoro atom;
R$^{5a}$ and R$^{5b}$ are independently selected from the group consisting of:
  a hydrogen atom, a fluoro atom, a chloro atom, a bromo atom, cyano, methyl-, methoxy-, difluoromethyl-, trifluoromethyl-, difluoromethoxy-, and trifluoromethoxy-; and
R$^6$ and R$^7$ are independently selected from the group consisting of:
  a hydrogen atom, a fluoro atom and a chloro atom,
or a salt thereof.

3. The compound of formula (I) according to claim 1, wherein:
R$^{5a}$ and R$^{5b}$ are each a hydrogen atom,
or a salt thereof.

4. The compound of formula (I) according to claim 1, wherein:
R$^1$ is a C$_1$-C$_6$-alkyl group,
  wherein said group is optionally substituted with one substituent selected from the group consisting of C$_1$-C$_3$-alkoxy, —NH$_2$, alkylamino-, dialkylamino-, and cyclic amines;
R$^2$ is the group

[structure]

R$^3$ is a hydrogen atom, a fluoro atom, a methyl- group or a trifluoromethyl- group;
R$^4$ is a hydrogen atom or a fluoro atom; and
R$^6$ and R$^7$ are independently selected from the group consisting of:
  a hydrogen atom, a fluoro atom and a chloro atom,
or a salt thereof.

5. The compound of formula (I) according to claim 1, wherein:
R$^6$ is selected from the group consisting of a hydrogen atom and a fluoro atom,
or a salt thereof.

6. The compound of formula (I) according to claim 1, wherein:
R$^7$ is a hydrogen atom,
or a salt thereof.

7. The compound of formula (I) according to claim 1, wherein:
R$^1$ is a C$_1$-C$_3$-alkyl group;
R$^2$ is the group

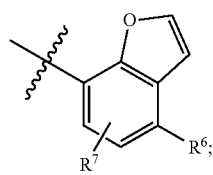

R$^3$ is a hydrogen atom, a fluoro atom, a methyl- group or a trifluoromethyl- group;
R$^4$ is a hydrogen atom;
R$^6$ is selected from the group consisting of a hydrogen atom, a fluoro atom and a chloro atom; and
R$^7$ is a hydrogen atom,
or a salt thereof.

8. The compound of formula (I) according to claim 1, wherein:
R$^1$ is a methyl group;
R$^2$ is the group

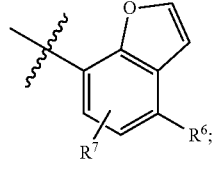

R$^3$ is a hydrogen atom, a fluoro atom, a methyl- group or a trifluoromethyl- group;
R$^4$ is a hydrogen atom;
R$^6$ is selected from the group consisting of a hydrogen atom and a fluoro atom; and
R$^7$ is a hydrogen atom,
or a salt thereof.

9. The compound of formula (I) according to claim 1, wherein:
R$^3$ is a fluoro atom, a methyl- group or a trifluoromethyl- group,
or a salt thereof.

10. The compound according to claim 1, which is selected from the group consisting of:
5-Fluoro-4-(4-fluoro-1-benzofuran-7-yl)-N-{4-[(methylsulfonyl)methyl]pyridin-2-yl}pyridin-2-amine;
5-Fluoro-4-(4-fluoro-1-benzofuran-7-yl)-N-{6-fluoro-4-[(methylsulfonyl)methyl]pyridin-2-yl}pyridin-2-amine;
5-Fluoro-4-(4-fluoro-1-benzofuran-7-yl)-N-{6-methyl-4-[(methylsulfonyl)methyl]pyridin-2-yl}pyridin-2-amine;
5-Fluoro-4-(4-fluoro-1-benzofuran-7-yl)-N-{4-[(methylsulfonyl)methyl]-6-(trifluoromethyl)pyridin-2-yl}pyridin-2-amine; and
4-(1-Benzofuran-7-yl)-5-fluoro-N-{4-[(methylsulfonyl)methyl]pyridin-2-yl}pyridin-2-amine,
or a salt thereof.

11. A method for treatment of lung carcinomas, prostate carcinomas, cervical carcinomas, colorectal carcinomas, melanomas or ovarian carcinomas comprising administering to a patient in need thereof a therapeutically effective amount of the compound according to claim 1, or a salt thereof.

12. A method for treatment of non-small cell lung carcinomas, hormone-independent human prostate carcinomas or multidrug-resistant human cervical carcinomas comprising administering to a patient in need thereof a therapeutically effective amount of the compound according to claim 1, or a salt thereof.

13. A pharmaceutical combination comprising the compound according to claim 1, or a salt thereof, in combination with at least one or more additional active ingredients.

14. A pharmaceutical composition comprising the compound according to claim 1, or a salt thereof, in combination with an inert, nontoxic, pharmaceutically suitable adjuvant.

15. A method for preparing the compound of formula (I) according to claim 1, comprising reacting a compound of formula 3

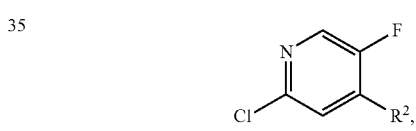

wherein R$^2$ and the substituents of R$^2$, which are R$^{5a}$, R$^{5b}$, R$^6$ and R$^7$, are defined as in claim 1, with a compound of formula 9,

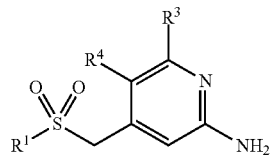

wherein R$^1$, R$^3$ and R$^4$ are defined as in claim 1, in a Palladium-catalysed C—N cross-coupling reaction,
to provide the compound of formula (I) according to claim 1,
and optionally reacting the compound of formula (I) according to claim 1 with a base or acid to yield a salt thereof.

* * * * *